US007033792B2

(12) United States Patent
Zhong et al.

(10) Patent No.: US 7,033,792 B2
(45) Date of Patent: Apr. 25, 2006

(54) ISOLATED HUMAN SECRETED PROTEINS, NUCLEIC ACID MOLECULES ENCODING HUMAN SECRETED PROTEINS, AND USES THEREOF

(75) Inventors: Jennifer Min Zhong, Rockville, MD (US); Chunhua Yan, Rockville, MD (US); Ellen M. Beasley, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 467 days.

(21) Appl. No.: 10/143,575

(22) Filed: May 13, 2002

(65) Prior Publication Data

US 2003/0166072 A1    Sep. 4, 2003

Related U.S. Application Data

(60) Provisional application No. 60/291,940, filed on May 21, 2001.

(51) Int. Cl.
*C12N 15/00* (2006.01)
(52) U.S. Cl. .................. 435/69.1; 435/320.1; 435/325; 536/23.1
(58) Field of Classification Search ............... 536/23.1; 435/320.1, 325, 70.1, 69.1
See application file for complete search history.

(56) References Cited

U.S. PATENT DOCUMENTS 6,461,850 B1  10/2002  Beasley et al.

FOREIGN PATENT DOCUMENTS

WO   PCT/US01/26345   7/2002

OTHER PUBLICATIONS

Results of BLAST search of SEQ ID NO:2 against Derwent (FastAlert and GeneSeqP) and NCBI (pataa) protein patent databases on Oct. 9, 2003.
Elaroussi et al. "A New Member to the Astasin Family of Metalloendopeptidases: a Novel 1,25-dihydroxyvitamin D-3 Stimulated mRNA From Chorioallantoic Membrane of Quail." Biocim Biophys Acta. Jan. 1994, vol. 1217, No. 1, pp. 1-8.
International Search report dated Jun. 23, 2003.
Elaroussi, Mahmoud A. et al. "A new member to the astasin family of metalloendopeptidases: A novel 1,25-dihydroxyvitamin D-3-stimulated mRNA from chorioallantoic membrane of quail." Biochimica et Biophysica Acta, vol. 1217 (1994) pp. 1-8.
-& Database EMBL'Online! Nov. 1, 1995, Elaroussi M.A. et al. "Astacin like metalloendopeptidase (EC 3.4.24.-)" Database accession No. P42662.
-& Database EMBL 'Online! Aug. 23, 1994, Elaroussi, M.A. et al. "Coturnix japonica astacin like metalloendopeptisade mRNA, complete cds." Database accession No. U12642; S68488.
Database EMBL 'Online!, Oct. 25, 1999, Sulston, J.E. et al. "*Homo sapiens* BAC clone RP11-574017 from 2, complete sequence." Database accession No. AC012307.
Database EMBL 'Online!, Jun. 18, 2001, Dias Neto, E. et al. "IL3-UT0117-070301-494-H12 UT0117 *Homo sapiens* cDNA, mRNA sequence." Database accession No. B1061462.
Yasumasu, Shigeki et al., "Isolation of cDNAs for LCE and HCE, Two Constituent Proteases of the Hatching Enzyme of *Oryzias latipes,* and Concurrent Expression of Their mRNAs during Development." Developmental Biology vol. 153 (1992), pp. 250-258, Tokyo, Japan.
-& Database EMBL 'Online!, Jul. 1, 1993, Yasumasu, S. et al. "High choriolytic enzyme 2 precursor (EC 3.4.24.67) (Hatching enzyme zinc-protease HCE 2 subunit) (Choriolysin H 2)." Database accession No. P31581.
-& Database EMBL 'Online!, Aug. 21, 1992, Yasumasu, S. et al. "*Oryzias latipes* hatching enzyme constituent protease (hce) mRNA, complete cds." Database accession No. M96171.
Database EMBL'Online!, Nov. 1, 1997 Eldering, J.A. et al. "Meprin A beta-subunit precursor (EC 3.4.24.18) (Endopeptidase-2) (N-benzoyl-L-tyrosyl-P-amino-benzoic acid hydrolase beta subunit) (PABA peptide hydrolase) (PPH beta)." Database accession No. Q16820.

*Primary Examiner*—Celine Qian
(74) *Attorney, Agent, or Firm*—Celera Genomics; Justin D. Karjala

(57) ABSTRACT

The present invention provides amino acid sequences of peptides that are encoded by genes within the human genome, the secreted peptides of the present invention. The present invention specifically provides isolated peptide and nucleic acid molecules, methods of identifying orthologs and paralogs of the secreted peptides, and methods of identifying modulators of the secreted peptides.

9 Claims, 11 Drawing Sheets

```
  1 ATGGAGGGTG TAGGGGGTCT CTGGCCTTGG GTGCTGGGTC TGCTCTCCTT
 51 GCCAGGTGTG ATCCTAGGAG CGCCCCTGGC CTCCAGCTGC GCAGGAGCCT
101 GTGGTACCAG CTTCCCAGAT GGCCTCACCC CTGAGGGAAC CCAGGCCTCC
151 GGGGACAAGG ACATTCCTGC AATTAACCAA GGGCTCATCC TGGAAGAAAC
201 CCCAGAGAGC AGCTTCCTCA TCGAGGGGGA CATCATCCGG CCGAGTCCCT
251 TCCGACTGCT GTCAGCAACC AGCAACAAAT GGCCCATGGG TGGTAGTGGT
301 GTCGTGGAGG TCCCCTTCCT GCTCTCCAGC AAGTACGATG AGCCCAGCCG
351 CCAGGTCATC CTGGAGGCTC TTGCGGAGTT TGAACGTTCC ACGTGCATCA
401 GGTTTGTCAC CTATCAGGAC CAGAGAGACT TCATTTCCAT CATCCCCATG
451 TATGGGTGCT TCTCGAGTGT GGGGCGCAGT GGAGGGATGC AGGTGGTCTC
501 CCTGGCGCCC ACGTGTCTCC AGAAGGGCCG GGGCATTGTC CTTCATGAGC
551 TCATGCATGT GCTGGGCTTC TGGCACGAGC ACACGCGGGC CGACCGGGAC
601 CGCTATATCC GTGTCAACTG GAACGAGATC CTGCCAGGCT TTGAAATCAA
651 CTTCATCAAG TCTCGGAGCA GCAAACATGCT GACGCCCTAT GACTACTCCT
701 CTGTGATGCA CTATGGGAGG CTCGCCTTCA GCCGGCGTGG GCTGCCCACC
751 ATCACACCAC TTTGGGCCCC CAGTGTCCAC ATCGGCCAGC GATGGAACCT
801 GAGTGCCTCG GACATCACCC GGGTCCTCAA ACTCTACGGC TGCAGCCCAA
851 GTGGCCCCAG GCCCCGTGGG AGAGGTGAGT GGCATGGCAG GAAGGTGACT
901 TGA (SEQ ID NO: 1)
```

FEATURES:
Start Codon: 1
Stop Codon: 901

Homologous proteins:

Sequences producing significant alignments:

| | Score (bits) | E Value |
|---|---|---|
| CRA\|18000005083809 /altid=gi\|2134006 /def=pir\|\|C48826 high chor... | 189 | 4e-47 |
| CRA\|18000005084876 /altid=gi\|2190297 /def=dbj\|BAA12146.1\| (D839... | 188 | 7e-47 |
| CRA\|18000004944034 /altid=gi\|399868 /def=sp\|P31581\|HCE2_ORYLA H... | 187 | 2e-46 |
| CRA\|18000004949282 /altid=gi\|399867 /def=sp\|P31580\|HCE1_ORYLA H... | 187 | 2e-46 |
| CRA\|18000004949557 /altid=gi\|400172 /def=sp\|P31579\|LCE_ORYLA LO... | 184 | 1e-45 |
| CRA\|18000005084877 /altid=gi\|2190298 /def=dbj\|BAA20403.1\| (D839... | 180 | 2e-44 |
| CRA\|18000004903374 /altid=gi\|1168541 /def=sp\|P42662\|ASTL_COTJA ... | 165 | 7e-40 |
| CRA\|18000005090083 /altid=gi\|2252655 /def=gb\|AAB62737.1\| (U6262... | 164 | 2e-39 |
| CRA\|18000005059455 /altid=gi\|2828509 /def=sp\|P42664\|UVS2_XENLA ... | 157 | 2e-37 |
| CRA\|18000005118725 /altid=gi\|2661464 /def=emb\|CAA05969.1\| (AJ00... | 155 | 5e-37 |

FIGURE 1

```
  1 MEGVGGLWPW VLGLLSLPGV ILGAPLASSC AGACGTSFPD GLTPEGTQAS
 51 GDKDIPAINQ GLILEETPES SFLIEGDIIR PSPFRLLSAT SNKWPMGGSG
101 WEVPFLLSS  KYDEPSRQVI LEALAEFERS TCIRFVTYQD QRDFISIIPM
151 YGCFSSVGRS GGMQWSLAP  TCLQKGRGIV LHELMHVLGF WHEHTRADRD
201 RYIRVNWNEI LPGFEINFIK SRSSNMLTPY DYSSVMHYGR LAFSRRGLPT
251 ITPLWAPSVH IGQRWNLSAS DITRVLKLYG CSPSGPRPRG RGEWHGRKVT
```
(SEQ ID NO:2)

FEATURES:
Functional domains and key regions:
PDOC00001 PS00001 ASN_GLYCOSYLATION
N-glycosylation site
   266-269  NLSA

---

PDOC00004 PS00004 CAMP_PHOSPHO_SITE
cAMP- and cGMP-dependent protein kinase phosphorylation site
   297-300  RKVT

---

PDOC00005 PS00005 PKC_PHOSPHO_SITE
Protein kinase C phosphorylation site
Number of matches: 3
  1  91-93  SNK
  2  109-111  SSK
  3  244-246  SRR

---

PDOC00006 PS00006 CK2_PHOSPHO_SITE
Casein kinase II phosphorylation site
Number of matches: 6
  1  37-40  SFPD
  2  110-113  SKYD
  3  137-140  TYQD
  4  195-198  TRAD
  5  228-231  TPYD
  6  268-271  SASD

---

PDOC00008 PS00008 MYRISTYL
N-myristoylation site
Number of matches: 6
  1  19-24  GVILGA
  2  32-37  GACGTS
  3  46-51  GTQASG
  4  152-157  GCFSSV
  5  262-267  GQRWNL
  6  280-285  GCSPSG

---

PDOC00009 PS00009 AMIDATION
Amidation site
   295-298  HGRK

---

PDOC00013 PS00013 PROKAR_LIPOPROTEIN
Prokaryotic membrane lipoprotein lipid attachment site
   20-30  VILGAPLASSC

---

PDOC00129 PS00142 ZINC_PROTEASE
Neutral zinc metallopeptidases, zinc-binding region signature
   179-188  IVLHELMHVL

FIGURE 2A

Membrane spanning structure and domains:
```
Helix Begin   End   Score  Certainty
  1      6    26    1.850  Certain
  2    143   163    0.849  Putative
```

BLAST Alignment to Top Hit:
>CRA|18000005083809 /altid=gi|2134006 /def=pir||C48826 high
        choriolytic hatching proteinase (EC 3.4.24.-) HCE21
        precursor - Japanese medaka /org=Japanese medaka
        /taxon=8090 /dataset=nraa /length=279
        Length = 279

Score = 189 bits (475), Expect = 4e-47
Identities = 106/272 (38%), Positives = 148/272 (53%), Gaps = 8/272 (2%)

```
Query:  14 LLSLPGVILGAPLASSCAGACGTSFPDGLTPEGTQASGDKDIPAINQGLILEETPESSFL  73
           LL L G+    P+ +       G   +G  EG +   + D         ++        L
Sbjct:  11 LLFLLGIAQALPVQNEEGHEEGNK--EGHGEEGVEEGDEDDFVDFTTRILTSNNNTDQLL  68

Query:  74 IEGDIIRPSPFRLLSATSNK--WPMGGSGVVEVPFLLSSKYDEPSRQVILEALAEFERST 131
           +EGD++ P+    +   N    W    +G V +P+++SS+Y        I  A+  F     T
Sbjct:  69 LEGDLVAPTNRNAMKCWYNSCFWKKASNGFWIPYVISSQYSRGEVATIEGAMRAFNGRT 128

Query: 132 CIRFVTYQDQRDFISIIPMYGCFSSVGRSGGMQVVSL-APTCLQKGRGIVLHELMHVLGF 190
           CIRFV    ++ DFIS++    GC+S +GR GG Q +SL      C+   G  I+ HEL H LGF
Sbjct: 129 CIRFVRRTNEYDFISVVSKNGCYSELGRKGGQQELSLNRGGCMYSG--IIQHELNHALGF 186

Query: 191 WHEHTRADRDRYIRVNWNEILPGFEINFIKSRSSNMLTPYDYSSVMHYGRLAFS-RRGLP 249
            HE TR+DRD Y+R+NW  I+P    NF K  ++N+ TPYDYSS+MHYGR AFS     G
Sbjct: 187 QHEQTRSDRDSYVRINWQNIIPASAYNFNKHDTNNLNTPYDYSSIMHYGRDAFSIAYGRD 246

Query: 250 TITPLWAPSVHIGQRWNLSASDITRVLKLYGC 281
           +ITP+  P+V IGQR +S DITR+ LY C
Sbjct: 247 SITPIPNPNVPIGQRNGMSRWDITRINVLYNC 278  (SEQ ID NO: 4)
```

>CRA|18000005084876 /altid=gi|2190297 /def=dbj|BAA12146.1| (D83950)
        choriolysin H [Oryzias latipes] /org=Oryzias latipes
        /taxon=8090 /dataset=nraa /length=266
        Length = 266

Score = 188 bits (473), Expect = 7e-47
Identities = 98/241 (40%), Positives = 141/241 (57%), Gaps = 6/241 (2%)

```
Query:  45 EGTQASGDKDIPAINQGLILEETPESSFLIEGDIIRPSPFRLLSATSNK--WPMGGSGVV 102
           EG +   + D  I  ++           L +EGD++ P+    +   S+    W   +G+V
Sbjct:  27 EGHEEGDEDDFVDITTRILTSNNNTDQLLLEGDLVAPTNRNAMKCWSSSCFWKKASNGLV 86

Query: 103 EVPFLLSSKYDEPSRQVILEALAEFERSTCIRFVTYQDQRDFISIIPMYGCFSSVGRSGG 162
            +P+++SS+Y        I  A+  F     TCIRFV    ++ DFIS++    GC+S +GR GG
Sbjct:  87 VIPYVISSEYSGGEVATIEGAMRAFNGKTCIRFVRRTNEYDFISVVSKTGCYSELGRKGG 146

Query: 163 MQVVSL-APTCLQKGRGIVLHELMHVLGFWHEHTRADRDRYIRVNWNEILPGFEINFIKS 221
            +Q +S+       C+   G  I+ HEL H LGF HE TR+DRD Y+R+NW  I+P    NF K
Sbjct: 147 LQELSINRGGCMYSG--IIQHELNHALGFQHEQTRSDRDSYVRINWENIIPASAYNFNKQ 204
```

FIGURE 2B

```
Query: 222 RSSNMLTPYDYSSVMHYGRLAFS-RRGLPTITPLWAPSVHIGQRWNLSASDITRVLKLYG 280
            ++N+ TPYDYSS+MHYG+ AFS   G +ITP+ P+V IGQR +S DITR+ LY
Sbjct: 205 DTNNLNTPYDYSSIMHYGKDAFSIAYGRDSITPIPNPNVPIGQRNGMSRWDITRINVLYN 264

Query: 281 C 281
            C
Sbjct: 265 C 265 (SEQ ID NO: 5)
```

Hmmer search results (Pfam):
Scores for sequence family classification (score includes all domains):

| Model | Description | Score | E-value | N |
|---|---|---|---|---|
| PF01400 | Astacin (Peptidase family M12A) | 275.0 | 5.9e-84 | 1 |
| CE00424 | E00424 meprin_A | 70.5 | 2.4e-18 | 1 |
| PF00712 | DNA polymerase III beta subunit | 2.9 | 7.8 | 1 |

Parsed for domains:

| Model | Domain | seq-f | seq-t | hmm-f | hmm-t | | score | E-value |
|---|---|---|---|---|---|---|---|---|
| PF00712 | 1/1 | 105 | 121 | 376 | 392 | .] | 2.9 | 7.8 |
| PF01400 | 1/1 | 92 | 283 | 1 | 200 | [] | 275.0 | 5.9e-84 |
| CE00424 | 1/1 | 179 | 284 | 142 | 252 | .. | 70.5 | 2.4e-18 |

FIGURE 2C

```
   1 TGCATGTCCT AATAAAGACT CTGTTTCTCT CCCCAAGCAG GGTGATTATT
  51 TCTTATCATT ATTTTAATTC TTTTGTTTTT TGAGACAGAG TCTCACTCTG
 101 TTGCCCAGGC TGGAGTGCAG TGGCACAATC TTGGCTCACT GCAACCTCTG
 151 CCTCCTGAGT TCAAGGGATT TCTGGCTAAT TTTTGTATTT TTAGTAGAGA
 201 TGGGGTTTCA CCGTGTTGGC TAGGCTGGTC TCGAACTCCT GACCTCAAGT
 251 AATCTGCCTG CCTTGGCCTC CCAAAATGCT GGGATTACAG GCATGAGCCA
 301 CTGCGCCCGG TCTACTTTAT TTTTTTTTAC TGAACATTCA TCTTTTTTTT
 351 TGAGATGGAG TCTCACTCTG TCCCCCGGGC TAGAGTGCAG TGGCGCGATT
 401 TTGGCTCATT GCAAACTCCA CCTCTGGGTT CAAGTGATTC ACCTGCCTCA
 451 GCCTCCCGAG TAGGTGGGAT TACAGGTGCC CGCCACCGTG CCCAGCTAAT
 501 TTTTGTATTC TTTTAGTAGA GATGGGGTTT CACCATGGTG GCCAGTCTGG
 551 TCTTGAATTC CTGACCTCGT GATCCACCTG CCTTGGCCTC CCAAAGTGCT
 601 GGGATTATAG GCGTGAGCCA CCGCGCCCTC CTGAACACTC ATCTTAAGTG
 651 GTCAGCCTTG TGCATTTGTT TTTTGATGGG TCCTATTCTT TATTTTACTT
 701 ATTTTTTCTA GGTTTACTGA GGCATAATCG ACAAATAAAA GTAGTATATG
 751 TTTAAGTATA CAACGTGATG TTTTGACATA TGCATACCTT GTGAAATGAT
 801 GACCACAACA AGCTAACTAG CATATCCATG GTGTGTATCC TGACATCTGT
 851 CAATACCCTG CCCTGGCAGC AGGGCGTCTG CCTCCATCAT GGTCTCCCTG
 901 TGATTCTGAT TCCTATCTTT GGAGAAGCTC TGGATTCCAG GCACAGTGGG
 951 AATGCTGAAA GGTCCTTGTG GACAATAGCT ATTCTTCTTG GCTCTGTCGC
1001 TTCCCTTCAC TGGGTGCAGG TGACTGTGGG GGTGTCCCCA AATGCTGCCC
1051 AGCGCTGACA TGCTCCGCCT CTGGGATTTC AATCCAGGTG GGGCCCTGAG
1101 TGACCTGGCT CTGGGGCTCA GGGGTATGGA GGAGGGGGGA TATAGGTAAG
1151 GAGTTTAAAT TTCCAAATCT GTGAAATGGG AATAAATACT GACTGATCAT
1201 GCCAGCTGCT GTGGGATTAG GGGGTGGACT CCCTGCGAGG CTCTGGGCAT
1251 CTGGGGGTTC CACCTTTCCC ACATGGCAGG CTTTCTAGGG TGCTGCACAC
1301 TGTTCAGTTT GTGAAATTTC CTGGAGCCCT GTGCTTGTGA TAGTGAACTT
1351 TTCTATATGT GTACTAAAAT AAAAGCTTGT GAAAGTGCAG TGACCTTTTC
1401 CTCCTTCCGG AGATACACGG GGGGCGCCCC AGGGTCTCAG GCAGCTTTCC
1451 CCATGTCTAA GCACAGGCCG GGGTAGGAAA GGGGGTCTCC CTCGCTGGAG
1501 GAATAGGTCT ATACCTGGGC TGGGGCCTCA GCTAGGCCTG GAGCAACTTT
1551 CTGCGATGTT TCTCTGCCCC CTGGAGGCAG GAAGGAACCT CATAAGAGCC
1601 ACACTCCCAA GCGGGCCCCT CCTGTCTTTC ACCTGCTACA GCCAGGAAGG
1651 GGACTGGGCT GGGGTGGGAA CCACAGGTAG GCATCGGAGG GGCTGCCAGT
1701 AGACCTGGTT TGGGTGGCGC TGCCGGTAGA GCTGGTTGGG GCGGGGCTGC
1751 AGGTGGAGCT GGTTGGGGCG GGGCTGCAGG TGGAGGTGGT TGGGGCGGGG
1801 CTGCAGGTGG AGATGGTTGG GGCGGGGCTG CAGGTGGAGG TGGTTGGGGC
1851 GGGGCTGCAG GTGGAGGCGG TTGAGGGGAG CAAGGTGGGA GGTGGAGCAG
1901 CTGCTATTTA AGAGGGGGTG GTGGTGCCGG TTCTGCAATT AGGTTACTGT
1951 GTCTTGCTGG GGCTTGGTCT TGTTTGCTGA AGGGGCAGCA GGGCTCTACC
2001 ATGGAGGGTG TAGGGGGTCT CTGGCCTTGG GTGCTGGGTC TGCTCTCCTT
2051 GCCAGGTAAG CTGGCTGCCT GTCCCTCCTG CTGCTGGCTC CAGCCTGGAG
2101 AAAGCTGGGG AGAGGCTAGA AGGTTGTGGC TGGAGCCTGC AGGGATTGTA
2151 GCTGAGCTCA GTAGCTCAGA GCACAGAGCT CTCCAGGGTT ATTCTAGAAG
2201 TCAGCTCCTG GGGGCCAAG GGGAGGCCTC CTGAAGGCCC TGGAAGCAGA
2251 GGGCCTGCCT GGCAGAAGAT AAGTGTTGTG CCCCAGGCCT ACTTGTCTTG
2301 GGGTGGGGGT AGGCTGTAAG TCCCCACTCC AGCCTGGTCA GGCAGGGAGT
2351 CATCCAGGCT GAGCCCATTG TCCAAGAGCC TGGGCTGAGA GAGAGTCATA
2401 AGGTGGGGTC TGAGGCTGGC CCTGCCCGTC ACGGGCGTCA GAACCCGAGG
2451 TCTGTCCTGC CTCCTTCCTT CCTGCCCCTC CTCTACCTCA TAGGTGGGGC
2501 ACATGGTCCC TTTTGGTCCC CCTAAGGGAG CTCCTTCCCT GAGGTCATCT
2551 AGACCTTGGC ACCAGTTGGG GTTGAGCAGG GAGGCTGGGA AGGCTCCTTG
2601 GCTTTGTGCT GGAGCCTACT CTTCCTAGGG ACTGAGTCTT ACCGTCTGAT
2651 CCCCCACACC CACCCCATGT CCTGCTGTCT GGTCTCACCG GTGGGTGCTC
2701 CAGGCATCTG TGTATGCCCC TGTCTGTCTG GACCAGGTGT GATCCTAGGA
2751 GCGCCCCTGG CCTCCAGCTG CGCAGGAGCC TGTGGTACCA GCTTCCCAGA
2801 TGGCCTCACC CCTGAGGGAA CCCAGGCCTC CGGGGACAAG GACATTCCTG
2851 CAATTAACCA AGGTGAGGGC ACTACATCTT CTCACGGCCT GGAGGGGCAC
2901 GACGTTATGT AGTGTGAAAA CCACACCGAA CACTCAGAAA TGCAGAGCCT
```

FIGURE 3A

```
2951 GGGAGGAAAT GGACCAGCTT ACTCTGGGCT CTAAGTGGTT TTTAAGAGAT
3001 GGAGTGGTGT TGCTATATTG CCCCGGCTGG TCTTGAACTC CTGGCCTTAA
3051 GTGATCTTCC TGCCTCTGCC TCCCGAGCAG CTGGGACTAC AGGTGTGAAT
3101 GGGTGGAAAT TCTATGGGCA ATTGCTTAAG TCTACTCTTT CTTTTTGTAT
3151 CTTTCTTAGT GGATTGTTAC TTTTATAAGA AAAACCAAGC TCTTAAAGGG
3201 CCTGGGCGTG GAGCTAAGCG GTTAGTCGCA GTCTGAGATT GTCAGCCACC
3251 CTGTGCAGGA CTGTCTGCAG GTGTGATTAA GAAGTCTGAA GCTCAGCTGG
3301 GTGCGGTGGC TCTCGCCTGT AGTCCCAGCA CTTTGGGAGG CTGAGGCGGG
3351 CAGATCATGA GGTCAGGAGA TCGAGACCAT CCTGGCTAAC ACAGTGAAAC
3401 CCCGTCCCCA CCAAAAATAC AAAAATTAGC CGGGCGTGGT GGCGGGCGCC
3451 TGTAGTCCCA GCTACTCAGG AGGCTGAGGC AGGAGAATGG CATGAACCTG
3501 GGAGGCGGAG CTTGCAGTGA GCTGAGATTG CGCCACTGCA CTCCAGCCTG
3551 GGCGACAGAG CATCTCACAA AAAACAAAAA ACAAAAGTCA GGCTCAGGGC
3601 CTTGCTGTCT GGGGATGTCA GCTGAGGAAT GAGGGTGTAT AAATAGCCTG
3651 AACAAAGCCA GTTGAAATGG AGACTGGAGT TCAGATGTTG GAGCAATGAG
3701 GGCTGAAGCA CTCAGGGTTG AAGCAATCGG GCTGAACAGG GGACAACCTT
3751 GCCCTAAGGG TGGGTGAGAT CCTACCAGAT GTGGTAGCCA CTGTGTGATC
3801 TGCCCCCTTC TTCCTCTGTG AGCTGACTTG GGAGCCCAGC GCCAGCTGAG
3851 CCTTGAGCCC CAGGCACCAT CCCACCCCTG GATCACCGTG AGTGGTCTGC
3901 AGGTAACCAG AACCAATGGA GAAAACTCCC AAATGCTGGT GACCCCAACA
3951 ACTATCCTAT CACCTACGGT GAGGCTGTCT CATAAGGGCT GCCCGTGCCT
4001 TACCCAGTGC TTTCCTGGGA AGCACCTGCC CATCTCCAGC CACTGTGAAT
4051 ATGGCTAATG CTGCACAGCT GTCTGCCTCC CAAAACTGGC CCTTGGCCAG
4101 AAGGAGCTGC CTCAGCCAGA GATGCCCGGG GGCTACTCCC TTGTCTGCCC
4151 AAGGTGGCCT ACTGTGACTT CTAAGGGACA GGAGTCTGGC TCCTGCCTAA
4201 AGGTGGTACA AGTCAGCGGT GTCATTTGTG GTCTGGAGCG CCCATGGGAT
4251 CTGGCTGAGG CTGTGCCTGG GTTCTTCCCT GCCTTCTCTC CTGCTTCCCT
4301 CACTCCCCCT GTGAGTCACT TGTGGGAGAC CCGGCTCAGG GAGAGATGAG
4351 AAGCAGAGGG ACTAAGAGGG GAGAGGGGCT TGCGAGAGCC GGTATTTGCC
4401 TGCCTCTGAT GGTGGAACAA ATTTGTGGAA CAAAATTGCC ACCTCAAGGG
4451 GCCTGAATAT AACAGATGGG TGGGGAATAG ATGGGGGATG AGGTGGGCAG
4501 GAGACCCCAG GGCCTGTTCT GAGGAGTGTG GCTCAGGCTG GAAGAAGCCA
4551 CTGCTTCCTG ACAGCAGGGA CCCGGGCTTG GGACTGGATT GCGTGGGTCA
4601 TGGGCTGTGT TTGAGCAGGG GAAGGCTGCA GTCCAGCCGA GAAGCCTTGC
4651 ACACTCAGGG ACTGTGTGAC TTCCCTGAGG CCACGCAGGC TCAGTGCTCA
4701 GGGAACCTCT AGCTCCACAG TCAGGAGAGG GACAGACCCC AAGCCTCAGT
4751 CTCCTTTGTC TTTGTCCTCC AGCCCCCTCA CACCTGCAGA CAGTCCGCAC
4801 AGGGTGGCTG ACATTCTCAA ACATCAACTA ATGACTTAAC TAAACACCCA
4851 GGCTCGGAGA GCCGATGACC TATACTTTTA TCAGGCTATT TAAGAACTTA
4901 TAAAAGTAAC AATCCACTAG GAAAGACACA AGAATAGACT TAAGTAAGTA
4951 GGGATTTGCT TGGCCTGTCC CACGAGTCAG TGTTCTGGGG GACATGGGCC
5001 AACACGTCCT TCTTCCTTTC CCAGGGCTCA TCCTGGAAGA AACCCCAGAG
5051 AGCAGCTTCC TCATCGAGGG GGACATCATC CGGCCGGTGA GTGCACACAC
5101 TGACGTGTGT GGGTGCGGAT AAGCCCACAG TTGGCGACAG GTCCTCTGAG
5151 CCCACCCTGG ATGCCATGGG GCCTGATGTG TGAGGGACAT ACATAGCTTG
5201 GTAGATGCCT CTTTTTGTCA AGGTCAGAGC GACTGTTCTG TTAGGAAATA
5251 GGAATAAGCC AGCCTGAATG CTAAGGAAGG CTGGTATCTG AAGTGCTGGC
5301 ACAGTCAGCC TGAGAGGGCT TCCTGAAGGA GGAGGTTTGA ACACTTGACC
5351 CAGCTTGGTA CCCTGCCCAG GGGAGGTGCT CAGCACTCGG GAGGTGCTCA
5401 GATAAAGGAA GAGATGAGCA AGGGTTGGCA GAGTGGCCAG TGGCAGATAA
5451 AGGGCCTGGT GGCAGTGGCG ACCTAGGGAT GGTGGAACAA GGAGTGATGT
5501 TGAGCCTGAC CATCTTGGCT GTGGTCGAGG GGCCGCATCT GAAGGGAGAA
5551 GGTTGCTGGG GATTGGGGCG CCTTGCTAAC AGAAAAGGGA ACACTGTGCC
5601 CAGGATGGCA GCCATGTGTT TCAGCAACT GCGAATGGCA GAAGGCTCCT
5651 GAATAGGACA GTGACCCAGG GGAAGGCAAG ACTGTCCTGT TGGAGGCTGC
5701 CACTGACGGC ACAGCCTCTG GCTGGGCAGG AGAGCCAGAG GCTGGCCCAA
5751 GGCTGCCCAG GAACTCCGGG GGCAGGGCAG ACCCTCTGGG TTATGCAGTG
5801 AGTGCTCGGG CAGGTGGTGT GCGACCACCC GGAGCAGAAT CAAATGCCTC
5851 CAGCCGATGG CACAGGCACG CTGGGGTGCT GTGGAGCCTG GGCACCGAAG
```

FIGURE 3B

```
5901 GGCTCTGGTT GCTGGAGAGC AGAAGTAAGC AGCCGAGGCC AGGGTGCTGC
5951 CTCACTTTCA CTCCATATGG CTCTGTTCCC ATGATCGTCC CATGTTCAGG
6001 GAAGCCTGGT GGCTGTTCCC CTCTGGAAGG GGCACTGTCA ACATGCTGGA
6051 GTGGGGCTGC TGGCCCAAGC CCTTCTGATT CAGGGCACCC TGGGGTGCTG
6101 GGCCTCCTAG CCAACATCCT CAGGGACTAA TCTCTTGTTT GCTTGAGATT
6151 GAAATTCTTT CATCATAGGC CAAGGGACTG TCTTGTGCAT CAAGGTTCAT
6201 GTAGCTGGCC CCTTGCCTTC CACAGCTCTG TCCCATCTCT AATGGTCCCC
6251 CATTCCCATG CACACAGGTC CTGACTCCCA CATCTTTGGG GTTCTGGTGC
6301 CCTGGGGTGT GGTACCCTTG GGCACAAAG CTTGGGTGGC CTCTGTCCCC
6351 AGGGGTTGAA CTGCTGCTCT CTCCTCAGAG TCCCTTCCGA CTGCTGTCAG
6401 CAACCAGCAA CAAATGGCCC ATGGGTGGTA GTGGTGTCGT GGAGGTCCCC
6451 TTCCTGCTCT CCAGCAAGTA CGGTGAGTGA GCATGGCGCG CTCCCTCCCT
6501 GCCTCAGCCC CTTCTTCCTA ATGCGGCAGG TGTTCCTCTC TTCCCTTTTC
6551 CTCTTACACC ATCACATCCC TTCCACCTCC CCACCCGAAG AACCTGTCCA
6601 CAGATGCCCT TCTGTTGCTG AAGGTCTCCT GAGTAGGGAG GGTTAAAATC
6651 TGATGGGAAG GTATGTCGAG TGGGATCTG GTTCCCCTTG AGACCATGCG
6701 GTGCAGAGGA CAGTGACCTA CCCAAGGCCA CACAGCCAGG GTCTGTCTGG
6751 GGCCCAGCTT CTTCCTGGCA CCACTAAGCT GCCCTTTCTT GATGCTATTT
6801 TGGGAGAGTG AGTTCAGAGC TCTGCTCCCA GACCCTCAGG TAGAGCTCAA
6851 AGACCACCAG GGCTCTGGGG GCTCAGCCAG GTGGTGTCTT CCAGATGAGC
6901 CCAGCCGGCCA GGTCATCCTG GAGGCTCTTG CGGAGTTTGA ACGTTCCACG
6951 TGCATCAGGT TTGTCACCTA TCAGGACCAG AGAGACTTCA TTTCCATCAT
7001 CCCCATGTAT GGGTAAGTGC CGGGGCCAGG ATGCGTATCT CAGCTCGCTT
7051 CTGCGTTCAG CCCGGAATTA ACTTGGCCAT TGTCTAAAAT GTATTCCTGG
7101 GCCCATCCTC CAGGGCTCAG TCTCCCTGCC CACCCTGAGG GGTCTGCCAA
7151 GTGTGAGCTG GACCTCCAGG GCGGAATGTG GGAAAGGGAT GGGAACGGTG
7201 CTAGACCCTC CATTTACAAA GCCCTCCTCT CCCGGGGGAC TCCATGAGGT
7251 GGTGAGGAGA GGAGGTTTTG CGGGGCAGAC AGTGCGTGAG TCACTGAGTC
7301 CTGGCAAGTC CCCTAACTTC TGAGCCTCTT CTGTCCCCTC TGGGGTGCGA
7351 GTGGTGGCGA TACCTGCTTC CTAGCTTGTC AGGGGCCTGA GGCAATTTGT
7401 GTGAAAGCCT TGGCTTAGGG CTGACCAGGA GGGTGTGCTC ACTTAGTAAG
7451 CTGCTTCTGT CCTCTGTGTT CATATATCAG TTTCTGCAGC CTCCCTGCAG
7501 CCCAGGCTGG TGATGGGGGT CCGGTATGGC CATTTCACAG AAGTCCAGGC
7551 AGTAAAGGGG CCTGGAGAAT GGTGAACCTG AGACTAGAGC CCAGAGTGGG
7601 GCCTGCCTGT TGGGAGTTTG TCTATCTTGT GTTGTGTGGG GAGGGAGAGC
7651 CCAGGTCTGT ATGTCCGGAG GGATCTGGGC TGGCACTTAC CCCACTTGCT
7701 CTCATCACCC TGCAGGTGCT TCTCGAGTGT GGGGCGCAGT GGAGGGATGC
7751 AGGTGGTCTC CCTGGCGCCC ACGTGTCTCC AGAAGGGCCG GGGCATTGTC
7801 CTTCATGAGC TCATGCATGT GCTGGGCTTC TGGCACGAGC ACACGCGGGC
7851 CGACCGGGAC CGCTATATCC GTGTCAACTG GAACGAGATC CTGCCAGGTG
7901 AGCCAGGCCA CACGCAGGAC AGGCTGGTGC CGGGGAGGGG ACAGCACGGC
7951 TTGGGCCCAA GTCGCCTGGT CCCCATGGGT GAGGCTATCC ATCCTCCCCA
8001 TCACCTGCCT GCTTCCTGTG GGGAAGGTGG GGGTCTCACT TCTGTCTGGT
8051 ACCTGGTACC TGGAGGTGGT ACTCTGGGTG CTGCTCTGGG CCCCAGGCCT
8101 TCCTCTACCC ACCTGTAGTT GTGCCTTAGC TAGGGCGCCA CCACCTGCTT
8151 TGTCTCGCTT CTCATCCCTG ACACTGTCCT CTCCCTGGCA ATGGGGCAGG
8201 CAGTGCCCAT GATACCTCCT TGTTGAGTAC TCTAGCAGCG GTCTCATGTA
8251 CCAGATACCA CCACCATGGA CTGGGGCTGT GTGCCAGCTT GGGGAGCTGA
8301 GCCAAAGTGG GACCCCAAGG TAGCAGGCTG CACAAGCCAA GTGCTGGGCC
8351 ACGGGCTGAG GGCAGCACTG TGGGCTGGG ACATGTGCCA GTGGTGCCAG
8401 TGAGCAGGCA GAAGGAACAC AGACTGTGGC CATGGGAGAG TGGAGGCTGG
8451 AGGCAGGTGG GCTGTGGTTC CTGTGCTGGC AGCGGCTGTG TGGCGCGGG
8501 GATCAGATCC TGGTGATGGT GGGGTCTCTC TCATTGTGGG CTTGATGGTC
8551 TGGTTCAGGA GGCAGGAAGA GCCCCACGAG GGAGGGGCAG AGGAGGTTTG
8601 GGTGGGAGTC TGGCTTAGGG GTTGGAGCAG GAAGGCCTAC CGCAGGTGGA
8651 GGGCGTCCAG CACGAGACCT TTCAGGGCTG TCATGTTAGC CAGGTGAGGC
8701 AGCCAGGGAA GCTGCCTGGG CCCAAGGACC TTCCCAGGCC CCAAACACCG
8751 CTTTCTCAGT GGCTCTCAGC AAACATGAGT CACAGAGAAA GGGGTGACGG
8801 GGCACGTGGG TAGCACCTCA CAAAGGGGGA GGGGATGGAT ATTGAATCAG
```

FIGURE 3C

```
 8851 ACCAGGCTGG GGAGGTTGTG AGGGGGGTGA CAAGTGACTC TGTACCCTGA
 8901 AAACAGACTG ATCCTTCCCA ATGCTCGTGG AACAGTTGTG AAAGTTTACC
 8951 CTGATAATTT TATGATATAC CATGAAATGC CATGAAAACC TGCAACTCTG
 9001 AAAGTAGACC AATGTAAACA TTCTGATCAT GATATAAAGT AGAAACCGAT
 9051 ACATCAAAAC CGAAAGCTTC TCCTATTCAG AAATTGAAAA AAACAACAAA
 9101 ACTTTCTTTC AGCTCTGGAG TTAAAGTACA GCAATTCTAA AAAAAAATCA
 9151 TGAAAGACTA GAAAAGCCAA TGGTTCACAG CTAAAGCAAT GCTCAGAGAA
 9201 AATGTGTAGA CTTACGTATC AGTAAACAGA ACAAATTGAG CATGTCAACC
 9251 CAAGTTAAAT GAAAGCAGGA GGGAATTTCA AAAGGTAAAA GCAGAAATTG
 9301 AGTTGGAAAA CAGCACTAAT AATTATTCCT AATGATAAAA CAGGCTAAAA
 9351 CACGGGTTCC CCAGTGGAAA AAATGAGAAC ATATTTGTTC CCATTTAGGT
 9401 TAATATGTTC TCATTAGGTT AACATGTACA GAAACTGCCA GGGCAGACAC
 9451 ATTAATAACA GTAATTAACT GTTGTGGGGC GGGGAGGTGG GAACTCAGGA
 9501 AGCAGGGGAT GGAATAGACT TTTACTACAT CTCAATATTT GACTTTTGAA
 9551 CCAAATGAAT ATACTACTTA TTCAAAAGTA TGTTTAATGA ATTTTTAAAA
 9601 AGAAGTAAGA GCTCAAGAGG CAGCTATGTT AGGCAGGTGG TGGGGTATGA
 9651 AGGTGCTGGA GGGCTCATTT GCTCCATGGA GAGGAAGCTG CTGTGACCGA
 9701 GGTGGCGTGT ATGCGTGGCT GGCTGGCTGG ATTTGGGAGG ATTGGGGGAG
 9751 CAATCCCTCT GAAGGCCTGG GGGACTTGAG TGAGGGGGAG ATGGGCTCCA
 9801 AATCTGGGGA AGTGTTGTGG CCTGACACAG GAAGAACAGG TGGGCCTGTG
 9851 ACTGGGGACT AGGGCATCAC CACTGCAGAT GACAGCGTGG CAGCTTTTTA
 9901 AAGCTGGGTC AAGGAATAGA CATTTCATCT GGGGTGGGAG GGACATCTGA
 9951 GACCCTGAGC AGTGTGGGAC CCGTGGCAGC TGTGGCTTAT GCAGAGACCA
10001 GCCCCGTGCA GACTGAATAT GCAAGGAGGA AGGATGGGTG GAGGGAACAG
10051 CTAGGAGGTG ATGGTTGGCC AGCCATGGGG TCCCTGTGCC TCTACCTCAA
10101 CTAGTACAGG TTGGGGATCC TCCCAGGGCT GGGAAAGTGG GACTGGTACC
10151 AGAAGCAGCA TGGTGGCTGT GGGCTCAGCC CCTCAGCTTG GGTGAGTTAT
10201 GAGCTCCCAG AAGACTCTCC CAGCCATTGC CTGCCCTTTC TTGCCTGCCC
10251 TCTTTATATA TCAGTAAGTT GTATTGTTTT TGTATTTTTA GGCTTTGAAA
10301 TCAACTTCAT CAAGTCTCGG AGCAGCAACA TGCTGACGCC CTATGACTAC
10351 TCCTCTGTGA TGCACTATGG GAGGTGAGGA CCCTGCCTTC TTCTCCCTCT
10401 GCTTCCCCCA GCCTCTCCCG TGGTGATCTG GACTCAGGGG TCTCCCGCTG
10451 GGTTCCAGGC TCGCCTTCAG CCGGCGTGGG CTGCCCACCA TCACACCACT
10501 TTGGGCCCCC AGTGTCCACA TCGGCCAGCG ATGGAACCTG AGTGCCTCGG
10551 ACATCACCCG GGTCCTCAAA CTCTACGGCT GCAGCCCAAG TGGCCCCAGG
10601 CCCCGTGGGA GAGGTGAGTG GCATGGCAGG AAGGTGACTT GAACCTGGAG
10651 AAGGCGCCTG TGCTCTAATG GTGTCAGGGA GGGTGACAAG GAGGGAGATG
10701 AGGTTGCAGG GGGAGCAGGG TGAGATCACG GGGGCTTGCC ACAACGACGC
10751 AGAACAAGCA CTTGAGGAAA GTTAACACTC ACTATGACTC AACTGTAACC
10801 AAAGAGGAAT AGGGCTCACT TGCTTAGCCT AGATAATAAA CATCTACCAA
10851 AAACCTAGAA CAAAAGTTAA GGGTAAAACA TTAAAACTGG GACCAAGACA
10901 AGTTTTCCCA CCATTGTCCC ATCTACTCCA CATTGTGTGG CAGTGGAGGT
10951 CCTGGGCACC GAGGTAGAGC CAAAGAAACT AAAGGTCCGA GGATTGGAAA
11001 GGAAGCAAAA AAATCGTTCA TAATAGATGA TTACCTGTAT TGAAAGCAAC
11051 AATCTATAAA CAAGTTATTA GAACTAATAA GAATTAGAAA AGGTAAATAC
11101 AGTTAATATA AAAATCATAT TTCTGTACAC CCAGTTAGAA AACACAATTG
11151 TTAGTAAACA TACCATTATA ATAGCAATCA TAAAGGTCCC AAGGAATAAA
11201 TCTGACAGCT GTATCAAACA TTTGAGGAAA AATGAACCTT TATTAAAATC
11251 GTTAAATAAT ACTTAAAATAT AGATAAATCT GTTATTGAAA GGAAGGCAAT
11301 GTTATAAAAA TTCAGTCTTC CCAAATTAAT CTATAAATTC CCACTCAAAA
11351 TAAGTTTGAT CTTGACAGAG TGATTTTTTT TTTCTTTTTT TTTTTTAAAG
11401 ATGGAGTCTC ACTCTGTCAC CCAGGCTGGA GTGCAGTGGC ACAATCTCGG
11451 CTCACTGCAG TCTCTGCCTC CGAGGTTCAA GTGATTCTTG TGCCTCAATC
11501 TCCTGAGCAG CTGGGCTTAC AGGTGCGTGC CACCACACCC AACTAATTTT
11551 TGTATTTTTA GTGGGGACAG GGTTTCACCA TGTTGGCCAG GCTGGTCTTG
11601 AACTCCTGAC CGCAAGTGAT GCGCCTGCCT TGGCCTCCCG ATTGACAGGG
11651 TGATTATAAA GTTTTTATAT GAGAATATGA AAGGTCAATA ATAGCCAAGA
11701 CATCCCTGAA GGAAAAACTA AAAGACTTG TCCTAGCAGA TGTTAGTCAT
11751 CTAGTTCATG AAACGTCTTT ACATAAATGC ATAGCACTGG AGCAAGGCTA
```

FIGURE 3D

```
11801 GACAATTGCC CGCTGGAACA GAATCAAATT TAGAAACAGA TTCCATTCAG
11851 AAGCAGAGCC TTGATGAAGG GCCATTGATG GTCACTATGG AAGGACAGTT
11901 AAGTTACTTA GTTGTCTTAG AGCCATTTAG CATCTATTTA AAAATCCCTA
11951 ACTCATATCA TGCGCAAATA ACTCTGGATG CATGAAAGAC ACATGTAATA
12001 AAAACTTTAA CATGTTTAGA AAAAAAATAT ATAGTAAGAT CTCTTCATGA
12051 CCTTGGGATA GGGAAGGATC ACTTAAATGA GATACAGCAC TAATTGTAAA
12101 ACTAGAAAGA TTCATAAATT CAACTACATT AATTATAACT TTGTCCAAAG
12151 GCACCAAAAA GAAAGTGAAA ATACAGGTTA CAAATAGACT TTTTTTTTTT
12201 TTTTTTGAGA CAGTTTCACT CTTTTTGCCC AGGCTGGAGT GCAATGGCAC
12251 GATCTTGGCT CACTGCAACT TCTGCCTCCC AGGTTCAAGT GATTCTCCTG
12301 CGTCAGCCTC CCTTGTAGCT GGGATTACAG TCACGCACCA CCATGCCTGG
12351 CTAATTTTGT ATTTTTATTA GAGATGGGGT TTCACCATGT TGGCTAGGCT
12401 GGTCTTGAGC TCCTGACCTC AGGTGATCCC CCTGCCTCAG CTTCCCAAAG
12451 TGCTGGGATT ACAGGTGTGA GCCACTGTGC CTGGCCCCAA TATATTTTTT
12501 TGCAACACAT AATTTGTATA CAAATACAT AAAGAACTAC ACATTAATAT
12551 AAGAACAAAC CAGCTGAGTG TGATGGCTCA TGCCTGTAAT CACAGCACTT
12601 TGGGAGGCTG AGGTGGGTGG ATCGCTTGAG CTTAGGAGTT C
```

FEATURES:
Start:     2001
Exon:      2001-2055
Intron:    2056-2736
Exon:      2737-2862
Intron:    2863-5024
Exon:      5025-5086
Intron:    5087-6378
Exon:      6379-6472
Intron:    6473-6894
Exon:      6895-7012
Intron:    7013-7715
Exon:      7716-7897
Intron:    7898-10291
Exon:      10292-10373
Intron:    10374-10458
Exon:      10459-10639
Stop:      10640

SNPs:

| DNA Position | Major | Minor | Domain | Protein Position | Major | Minor |
|---|---|---|---|---|---|---|
| 70 | C | A | Beyond ORF(5') | | | |
| 5759 | A | G | Intron | | | |
| 9859 | C | A | Intron | | | |
| 10232 | T | C | Intron | | | |
| 10319 | G | A | Exon | 222 | R | Q |
| 12631 | C | – | Beyond ORF(3') | | | |

FIGURE 3E

Context:

DNA
Position

70     TGCATGTCCTAATAAAGACTCTGTTTCTCTCCCCAAGCAGGGTGATTATTTCTTATCATT
       ATTTTAATT
       [C,A]
       TTTTGTTTTTTGAGACAGAGTCTCACTCTGTTGCCCAGGCTGGAGTGCAGTGGCACAATC
       TTGGCTCACTGCAACCTCTGCCTCCTGAGTTCAAGGGATTTCTGGCTAATTTTTGTATTT
       TTAGTAGAGATGGGGTTTCACCGTGTTGGCTAGGCTGGTCTCGAACTCCTGACCTCAAGT
       AATCTGCCTGCCTTGGCCTCCCAAAATGCTGGGATTACAGGCATGAGCCACTGCGCCCGG
       TCTACTTTATTTTTTTTTACTGAACATTCATCTTTTTTTTTGAGATGGAGTCTCACTCTG

5759   GTGGCAGTGGCGACCTAGGGATGGTGGAACAAGGAGTGATGTTGAGCCTGACCATCTTGG
       CTGTGGTCGAGGGGCCGCATCTGAAGGGAGAAGGTTGCTGGGGATTGGGGCGCCTTGCTA
       ACAGAAAAGGGAACACTGTGCCCAGGATGGCAGCCATGTGTTTCAGGCAACTGCGAATGG
       CAGAAGGCTCCTGAATAGGACAGTGACCCAGGGGAAGGCAAGACTGTCCTGTTGGAGGCT
       GCCACTGACGGCACAGCCTCTGGCTGGGCAGGAGAGCCAGAGGCTGGCCCAAGGCTGCCC
       [A,G]
       GGAACTCCGGGGGCAGGGCAGACCCTCTGGGTTATGCAGTGAGTGCTCGGGCAGGTGGTG
       TGCGACCACCCGGAGCAGAATCAAATGCCTCCAGCCGATGGCACAGGCACGCTGGGGTGC
       TGTGGAGCCTGGGCACCGAAGGGCTCTGGTTGCTGGAGAGCAGAAGTAAGCAGCCGAGGC
       CAGGGTGCTGCCTCACTTTCACTCCATATGGCTCTGTTCCCATGATCGTCCCATGTTCAG
       GGAAGCCTGGTGGCTGTTCCCCTCTGGAAGGGGCACTGTCAACATGCTGGAGTGGGGCTG

9859   ATATACTACTTATTCAAAAGTATGTTTAATGAATTTTTAAAAAGAAGTAAGAGCTCAAGA
       GGCAGCTATGTTAGGCAGGTGGTGGGGTATGAAGGTGCTGGAGGGCTCATTTGCTCCATG
       GAGAGGAAGCTGCTGTGACCGAGGTGGCGTGTATGCGTGGCTGGCTGGCTGGATTTGGGA
       GGATTGGGGGAGCAATCCCTCTGAAGGCCTGGGGGACTTGAGTGAGGGGGAGATGGGCTC
       CAAATCTGGGGAAGTGTTGTGGCCTGACACAGGAAGAACAGGTGGGCCTGTGACTGGGGA
       [C,A]
       TAGGGCATCACCACTGCAGATGACAGCGTGGCAGCTTTTTAAAGCTGGGTCAAGGAATAG
       ACATTTCATCTGGGGTGGGAGGGACATCTGAGACCCTGAGCAGTGTGGGACCCGTGGCAG
       CTGTGGCTTATGCAGAGACCAGCCCCGTGCAGACTGAATATGCAAGGAGGAAGGATGGGT
       GGAGGGAACAGCTAGGAGGTGATGGTTGGCCAGCCATGGGGTCCCTGTGCCTCTACCTCA
       ACTAGTACAGGTTGGGGATCCTCCCAGGGCTGGGAAAGTGGGACTGGTACCAGAAGCAGC

10232  GGGTGGGAGGGACATCTGAGACCCTGAGCAGTGTGGGACCCGTGGCAGCTGTGGCTTATG
       CAGAGACCAGCCCCGTGCAGACTGAATATGCAAGGAGGAAGGATGGGTGGAGGGAACAGC
       TAGGAGGTGATGGTTGGCCAGCCATGGGGTCCCTGTGCCTCTACCTCAACTAGTACAGGT
       TGGGGATCCTCCCAGGGCTGGGAAAGTGGGACTGGTACCAGAAGCAGCATGGTGGCTGTG
       GGCTCAGCCCCTCAGCTTGGGTGAGTTATGAGCTCCCAGAAGACTCTCCCAGCCATTGCC
       [T,C]
       GCCCTTTCTTGCCTGCCCTCTTTATATATCAGTAAGTTGTATTGTTTTTGTATTTTTAGG
       CTTTGAAATCAACTTCATCAAGTCTCGGAGCAGCAACATGCTGACGCCCTATGACTACTC
       CTCTGTGATGCACTATGGGAGGTGAGGACCCTGCCTTCTTCTCCCTCTGCTTCCCCCAGC
       CTCTCCCGTGGTGATCTGGACTCAGGGGTCTCCCGCTGGGTTCCAGGCTCGCCTTCAGCC
       GGCGTGGGCTGCCCACCATCACACCACTTTGGGCCCCCAGTGTCCACATCGGCCAGCGAT

10319  ATGCAAGGAGGAAGGATGGGTGGAGGGAACAGCTAGGAGGTGATGGTTGGCCAGCCATGG
       GGTCCCTGTGCCTCTACCTCAACTAGTACAGGTTGGGGATCCTCCCAGGGCTGGGAAAGT
       GGGACTGGTACCAGAAGCAGCATGGTGGCTGTGGGCTCAGCCCCTCAGCTTGGGTGAGTT
       ATGAGCTCCCAGAAGACTCTCCCAGCCATTGCCTTGCCCTTTCTTGCCTGCCCTCTTTATA
       TATCAGTAAGTTGTATTGTTTTTGTATTTTTAGGCTTTGAAATCAACTTCATCAAGTCTC
       [G,A]
       GAGCAGCAACATGCTGACGCCCTATGACTACTCCTCTGTGATGCACTATGGGAGGTGAGG
       ACCCTGCCTTCTTCTCCCTCTGCTTCCCCCAGCCTCTCCCGTGGTGATCTGGACTCAGGG

FIGURE 3F

```
              GTCTCCCGCTGGGTTCCAGGCTCGCCTTCAGCCGGCGTGGGCTGCCCACCATCACACCAC
              TTTGGGCCCCCAGTGTCCACATCGGCCAGCGATGGAACCTGAGTGCCTCGGACATCACCC
              GGGTCCTCAAACTCTACGGCTGCAGCCCAAGTGGCCCCAGGCCCCGTGGGAGAGGTGAGT

12631         TCACGCACCACCATGCCTGGCTAATTTTTGTATTTTTATTAGAGATGGGGTTTCACCATGT
              TGGCTAGGCTGGTCTTGAGCTCCTGACCTCAGGTGATCCCCCTGCCTCAGCTTCCCAAAG
              TGCTGGGATTACAGGTGTGAGCCACTGTGCCTGGCCCCAATATATTTTTTTGCAACACAT
              AATTTGTATACAAAATACATAAAGAACTACACATTAATATAAGAACAAACCAGCTGAGTG
              TGATGGCTCATGCCTGTAATCACAGCACTTTGGGAGGCTGAGGTGGGTGGATCGCTTGAG
              [C,-]
              TTAGGAGTTC
```

FIGURE 3G

SEQUENCE LISTING

<160> NUMBER OF SEQ ID NOS: 5

<210> SEQ ID NO 1
<211> LENGTH: 903
<212> TYPE: DNA
<213> ORGANISM: Homo sapiens

<400> SEQUENCE: 1

```
atggaggtg taggggtct ctggccttgg gtgctgggtc tgctctcctt gccaggtgtg      60
atcctaggag cgcccctggc ctccagctgc gcaggagcct gtggtaccag cttcccagat     120
ggcctcaccc ctgagggaac ccaggcctcc ggggacaagg acattcctgc aattaaccaa     180
gggctcatcc tggaagaaac cccagagagc agcttcctca tcgaggggga catcatccgg     240
ccgagtccct tccgactgct gtcagcaacc agcaacaaat ggcccatggg tggtagtggt     300
gtcgtggagg tccccttcct gctctccagc aagtacgatg agcccagccg ccaggtcatc     360
ctggaggctc ttgcggagtt tgaacgttcc acgtgcatca ggtttgtcac ctatcaggac     420
cagagagact tcatttccat catccccatg tatgggtgct tctcgagtgt ggggcgcagt     480
ggagggatgc aggtggtctc cctggcgccc acgtgtctcc agaagggccg gggcattgtc     540
cttcatgagc tcatgcatgt gctgggcttc tggcacgagc acacgcgggc cgaccgggac     600
cgctatatcc gtgtcaactg gaacgagatc ctgccaggct ttgaaatcaa cttcatcaag     660
tctcggagca gcaacatgct gacgccctat gactactcct ctgtgatgca ctatgggagg     720
ctcgccttca gccggcgtgg gctgcccacc atcacaccac tttgggcccc cagtgtccac     780
atcggccagc gatggaacct gagtgcctcg gacatcaccc gggtcctcaa actctacggc     840
tgcagcccaa gtggccccag gccccgtggg agaggtgagt ggcatggcag gaaggtgact     900
tga                                                                  903
```

<210> SEQ ID NO 2
<211> LENGTH: 300
<212> TYPE: PRT
<213> ORGANISM: Homo sapiens

<400> SEQUENCE: 2

Met Glu Gly Val Gly Gly Leu Trp Pro Trp Val Leu Gly Leu Leu Ser
1               5                   10                  15

Leu Pro Gly Val Ile Leu Gly Ala Pro Leu Ala Ser Ser Cys Ala Gly
            20                  25                  30

Ala Cys Gly Thr Ser Phe Pro Asp Gly Leu Thr Pro Glu Gly Thr Gln

-continued

```
                35                  40                  45
Ala Ser Gly Asp Lys Asp Ile Pro Ala Ile Asn Gln Gly Leu Ile Leu
 50                  55                  60

Glu Glu Thr Pro Glu Ser Ser Phe Leu Ile Glu Gly Asp Ile Ile Arg
 65                  70                  75                  80

Pro Ser Pro Phe Arg Leu Leu Ser Ala Thr Ser Asn Lys Trp Pro Met
                 85                  90                  95

Gly Gly Ser Gly Val Val Glu Val Pro Phe Leu Leu Ser Ser Lys Tyr
                100                 105                 110

Asp Glu Pro Ser Arg Gln Val Ile Leu Glu Ala Leu Ala Glu Phe Glu
            115                 120                 125

Arg Ser Thr Cys Ile Arg Phe Val Thr Tyr Gln Asp Gln Arg Asp Phe
130                 135                 140

Ile Ser Ile Ile Pro Met Tyr Gly Cys Phe Ser Ser Val Gly Arg Ser
145                 150                 155                 160

Gly Gly Met Gln Val Val Ser Leu Ala Pro Thr Cys Leu Gln Lys Gly
                165                 170                 175

Arg Gly Ile Val Leu His Glu Leu Met His Val Leu Gly Phe Trp His
            180                 185                 190

Glu His Thr Arg Ala Asp Arg Asp Arg Tyr Ile Arg Val Asn Trp Asn
        195                 200                 205

Glu Ile Leu Pro Gly Phe Glu Ile Asn Phe Ile Lys Ser Arg Ser Ser
210                 215                 220

Asn Met Leu Thr Pro Tyr Asp Tyr Ser Ser Val Met His Tyr Gly Arg
225                 230                 235                 240

Leu Ala Phe Ser Arg Arg Gly Leu Pro Thr Ile Thr Pro Leu Trp Ala
                245                 250                 255

Pro Ser Val His Ile Gly Gln Arg Trp Asn Leu Ser Ala Ser Asp Ile
            260                 265                 270

Thr Arg Val Leu Lys Leu Tyr Gly Cys Ser Pro Ser Gly Pro Arg Pro
        275                 280                 285

Arg Gly Arg Gly Glu Trp His Gly Arg Lys Val Thr
290                 295                 300

<210> SEQ ID NO 3
<211> LENGTH: 12641
<212> TYPE: DNA
<213> ORGANISM: Homo sapiens

<400> SEQUENCE: 3
tgcatgtcct aataaagact ctgtttctct ccccaagcag ggtgattatt tcttatcatt     60
attttaattc ttttgttttt tgagacagag tctcactctg ttgcccaggc tggagtgcag    120
tggcacaatc ttggctcact gcaacctctg cctcctgagt tcaagggatt tctggctaat    180
ttttgtattt ttagtagaga tggggtttca ccgtgttggc taggctggtc tcgaactcct    240
gacctcaagt aatctgcctg ccttggcctc ccaaaatgct gggattacag gcatgagcca    300
ctgcgcccgg tctactttat ttttttttac tgaacattca tcttttttt tgagatggag    360 tctcactctg tcccccgggc tagagtgcag tggcgcgatt ttggctcatt gcaaactcca    420
cctctgggtt caagtgattc acctgcctca gcctcccgag taggtgggat tacaggtgcc    480
cgccaccgtg cccagctaat ttttgtattc ttttagtaga gatgggtttt caccatggtg    540
gccagtctgg tcttgaattc ctgacctcgt gatccacctg ccttggcctc ccaaagtgct    600
gggattatag gcgtgagcca ccgcgccctc ctgaacactc atcttaagtg gtcagccttg    660
```

```
tgcatttgtt ttttgatggg tcctattctt tattttactt attttttcta ggtttactga    720
ggcataatcg acaaataaaa gtagtatatg tttaagtata caacgtgatg ttttgacata    780
tgcataccct gtgaaatgat gaccacaaca agctaactag catatccatg gtgtgtatcc    840
tgacatctgt caatacccct ccctggcagc agggcgtctg cctccatcat ggtctccctg    900
tgattctgat tcctatcttt ggagaagctc tggattccag gcacagtggg aatgctgaaa    960
ggtccttgtg gacaatagct attcttcttg gctctgtcgc ttcccttcac tgggtgcagg   1020
tgactgtggg ggtgtcccca aatgctgccc agcgctgaca tgctccgcct ctgggatttc   1080
aatccaggtg gggccctgag tgacctggct ctggggctca ggggtatgga ggagggggga   1140
tataggtaag gagtttaaat ttccaaatct gtgaaatggg aataaatact gactgatcat   1200
gccagctgct gtgggattag ggggtggact ccctgcgagg ctctgggcat ctggggttc    1260 cacctttccc acatggcagg ctttctaggg tgctgcacac tgttcagttt gtgaaatttc   1320
ctggagccct gtgcttgtga tagtgaactt ttctatatgt gtactaaaat aaaagcttgt   1380
gaaagtgcag tgacctttc  ctccttccgg agatacacgg gggcgcccc  aggtctcag    1440 gcagctttcc ccatgtctaa gcacaggccg gggtaggaaa ggggtctcc  ctcgctggag   1500 gaataggtct atacctgggc tggggcctca gctaggcctg gagcaacttt ctgcgatgtt   1560
tctctgcccc ctggaggcag gaaggaacct cataagagcc acactcccaa gcgggcccct   1620
cctgtctttc acctgctaca gccaggaagg ggactgggct ggggtgggaa ccacaggtag   1680
gcatcggagg ggctgccagt agacctggtt tgggtggcgc tgccggtaga gctggttggg   1740
gcggggctgc aggtggagct ggttgggcg  gggctgcagg tggaggtggt tggggcgggg   1800
ctgcaggtga gatggttgg  ggcggggctg caggtggagg tggttgggc  ggggctgcag   1860 gtggaggcgg ttgaggggag caaggtggga ggtggagcag ctgctattta gaggggtg    1920 gtggtgccgg ttctgcaatt aggttactgt gtcttgctgg ggcttggtct tgtttgctga   1980
aggggcagca gggctctacc atggagggtg taggggtct  ctggccttgg gtgctgggtc   2040
tgctctcctt gccaggtaag ctggctgcct gtccctcctg ctgctggctc cagcctggag   2100
aaagctgggg agaggctaga aggttgtggc tggagcctgc agggattgta gctgagctca   2160
gtagctcaga gcacagagct ctccagggtt attctagaag tcagtcctg  gggggccaag   2220 gggaggcctc ctgaaggccc tggaagcaga gggcctgcct ggcagaagat aagtgttgtg   2280
ccccaggcct acttgtcttg gggtgggggt aggctgtaag tccccactcc agcctggtca   2340
ggcagggagt catccaggct gagcccattg tccaagagcc tgggctgaga gagtcata    2400 aggtgggtc  tgaggctggc cctgcccgtc acgggcgtca gaacccgagg tctgtcctgc   2460
ctccttcctt cctgcccctc tctacctca  taggtgggc  acatggtccc ttttggtccc   2520
cctaagggag ctccttccct gaggtcatct agaccttggc accagttggg gttgagcagg   2580
gaggctggga aggctccttg gctttgtgct ggagcctact cttcctaggg actgagtctt   2640
accgtctgat cccccacacc caccccatgt cctgctgtct ggtctcaccg gtgggtgctc   2700
caggcatctg tgtatgcccc tgtctgtctg gaccaggtgt gatcctagga gcgcccctgg   2760
cctccagctg cgcaggagcc tgtggtacca gcttcccaga tggcctcacc cctgagggaa   2820
cccaggcctc cggggacaag gacattcctg caattaacca aggtgagggc actacatctt   2880 ctcacgcct  ggaggggcac gacgttatgt agtgtgaaaa ccacaccgaa cactcagaaa   2940
tgcagagcct gggaggaaat ggaccagctt actctgggct ctaagtggtt tttaagagat   3000
```

-continued

```
ggagtggtgt tgctatattg ccccggctgg tcttgaactc ctggccttaa gtgatcttcc    3060
tgcctctgcc tcccgagcag ctgggactac aggtgtgaat gggtggaaat tctatgggca    3120
attgcttaag tctactcttt cttttgtat ctttcttagt ggattgttac ttttataaga     3180
aaaaccaagc tcttaaaggg cctgggcgtg agctaagcg gttagtcgca gtctgagatt     3240
gtcagccacc ctgtgcagga ctgtctgcag gtgtgattaa gaagtctgaa gctcagctgg    3300
gtgcggtggc tctcgcctgt agtcccagca ctttgggagg ctgaggcggg cagatcatga    3360
ggtcaggaga tcgagaccat cctggctaac acagtgaaac cccgtcccca ccaaaaatac    3420
aaaaattagc cgggcgtggt ggcgggcgcc tgtagtccca gctactcagg aggctgaggc    3480
aggagaatgg catgaacctg ggaggcggag cttgcagtga gctgagattg cgccactgca    3540
ctccagcctg ggcgacagag catctcacaa aaaacaaaaa acaaaagtca ggctcagggc    3600
cttgctgtct ggggatgtca gctgaggaat gagggtgtat aaatagcctg aacaaagcca    3660
gttgaaatgg agactggagt tcagatgttg agcaatgag gctgaagca ctcaggttg       3720 aagcaatcgg gctgaacagg gacaaccttt gccctaaggg tgggtgagat cctaccagat    3780
gtggtagcca ctgtgtgatc tgccccttc ttcctctgtg agctgacttg ggagcccagc     3840
gccagctgag ccttgagccc caggcaccat cccaccctg gatcaccgtg agtggtctgc     3900
aggtaaccag aaccaatgga gaaaactccc aaatgctggt gaccccaaca actatcctat    3960
cacctacggt gaggctgtct cataagggct gcccgtgcct tacccagtgc tttcctggga    4020
agcacctgcc catctccagc cactgtgaat atggctaatg ctgcacagct gtctgcctcc    4080
caaaactggc ccttggccag aaggagctgc ctcagccaga gatgcccggg ggctactccc    4140
ttgtctgccc aaggtggcct actgtgactt ctaagggaca ggagtctggc tcctgcctaa    4200
aggtggtaca agtcagcggt gtcatttgtg gtctggagcg cccatgggat ctggctgagg    4260
ctgtgcctgg gttcttccct gccttctctc ctgcttccct cactcccct gtgagtcact     4320 tgtgggagac ccggctcagg gagagatgag aagcagaggg actaagaggg gagaggggct    4380
tgcgagagcc ggtatttgcc tgcctctgat ggtggaacaa atttgtggaa caaaattgcc    4440
acctcaaggg gcctgaatat aacagatggg tggggaatag atgggggatg aggtgggcag    4500
gagaccccag ggcctgttct gaggagtgtg gctcaggctg gaagaagcca ctgcttcctg    4560
acagcaggga cccgggcttg ggactggatt gcgtgggtca tgggctgtgt ttgagcaggg    4620
gaaggctgca gtccagccga gaagccttgc acactcaggg actgtgtgac ttccctgagg    4680
ccacgcaggc tcagtgctca gggaacctct agctccacag tcaggagagg gacagacccc    4740
aagcctcagt ctcctttgtc tttgtcctcc agccccctca cacctgcaga cagtccgcac    4800
agggtggctg acattctcaa acatcaacta atgacttaac taaacaccca ggctcggaga    4860
gccgatgacc tatacttta tcaggctatt taagaactta taaaagtaac aatccactag     4920
gaaagacaca agaatagact taagtaagta gggatttgct tggcctgtcc cacgagtcag    4980
tgttctgggg gacatgggcc aacacgtcct tcttcctttc ccagggctca tcctggaaga    5040
aaccccagag agcagcttcc tcatcgaggg ggacatcatc cggccggtga gtgcacacac    5100
tgacgtgtgt gggtgcggat aagcccacag ttggcgacag gtcctctgag cccaccctgg    5160
atgccatggg gcctgatgtg tgaggacat acatagcttg gtagatgcct ctttttgtca    5220
aggtcagagc gactgttctg ttaggaaata ggaataagcc agcctgaatg ctaaggaagg    5280
ctggtatctg aagtgctggc acagtcagcc tgagagggct tcctgaagga ggaggtttga    5340
acacttgacc cagcttggta ccctgcccag gggaggtgct cagcactcgg gaggtgctca    5400
```

-continued

```
gataaaggaa gagatgagca agggttggca gagtggccag tggcagataa agggcctggt    5460
ggcagtggcg acctagggat ggtggaacaa ggagtgatgt tgagcctgac catcttggct    5520
gtggtcgagg ggccgcatct gaagggagaa ggttgctggg gattggggcg ccttgctaac    5580
agaaaaggga acactgtgcc caggatggca gccatgtgtt tcaggcaact gcgaatggca    5640
gaaggctcct gaataggaca gtgacccagg ggaaggcaag actgtcctgt tggaggctgc    5700
cactgacggc acagcctctg ctgggcagga gagccagag gctggcccaa ggctgcccag    5760
gaactccggg ggcagggcag accctctggg ttatgcagtg agtgctcggg caggtggtgt    5820
gcgaccaccc ggagcagaat caaatgcctc cagccgatgg cacaggcacg ctggggtgct    5880
gtggagcctg ggcaccgaag ggctctggtt gctggagagc agaagtaagc agccgaggcc    5940
agggtgctgc ctcactttca ctccatatgg ctctgttccc atgatcgtcc catgttcagg    6000
gaagcctggt ggctgttccc ctctggaagg ggcactgtca acatgctgga gtggggctgc    6060
tggcccaagc ccttctgatt cagggcaccc tggggtgctg ggcctcctag ccaacatcct    6120
cagggactaa tctcttgttt gcttgagatt gaaattcttt catcataggc caagggactg    6180
tcttgtgcat caaggttcat gtagctggcc ccttgccttc cacagctctg tcccatctct    6240
aatggtcccc cattcccatg cacacaggtc ctgactccca catctttggg gttctggtgc    6300
cctggggtgt ggtacccttg gggcacaaag cttggtggc ctctgtcccc agggggttgaa    6360 ctgctgctct ctcctcagag tcccttccga ctgctgtcag caaccagcaa caaatggccc    6420
atgggtggta gtggtgtcgt ggaggtcccc ttcctgctct ccagcaagta cggtgagtga    6480
gcatggcgcg ctccctccct gcctcagccc cttcttccta atgcggcagg tgttcctctc    6540
ttcccttttc ctcttacacc atcacatccc ttccacctcc ccacccgaag aacctgtcca    6600
cagatgccct tctgttgctg aaggtctcct gagtagggag ggttaaaatc tgatgggaag    6660
gtatgtcgag tggggatctg gttccccttg agaccatgcg gtgcagagga cagtgaccta    6720
cccaaggcca cacagccagg gtctgtctgg ggcccagctt cttcctggca ccactaagct    6780
gccctttctt gatgctattt tgggagagtg agttcagagc tctgctccca gaccctcagg    6840
tagagctcaa agaccaccag ggctctgggg gctcagccag gtggtgtctt ccagatgagc    6900
ccagccgcca ggtcatcctg gaggctcttg cggagtttga acgttccacg tgcatcaggt    6960
ttgtcaccta tcaggaccag agagacttca tttccatcat ccccatgtat gggtaagtgc    7020
cggggccagg atgcgtatct cagctcgctt ctgcgttcag cccggaatta acttggccat    7080
tgtctaaaat gtattcctgg gcccatcctc cagggctcag tctccctgcc caccctgagg    7140
ggtctgccaa gtgtgagctg gacctccagg gcggaatgtg ggaaagggat gggaacggtg    7200
ctagaccctc catttacaaa gccctcctct cccgggggac tccatgaggt ggtgaggaga    7260
ggaggttttg cggggcagac agtgcgtgag tcactgagtc ctggcaagtc ccctaacttc    7320
tgagcctctt ctgtcccctc tggggtgcga gtggtggcga tacctgcttc ctagcttgtc    7380
aggggcctga ggcaatttgt gtgaaagcct tggcttaggg ctgaccagga gggtgtgctc    7440
acttagtaag ctgcttctgt cctctgtgtt catatatcag tttctgcagc ctccctgcag    7500
cccaggctgg tgatggggt ccggtatggc catttcacag aagtccaggc agtaaagggg    7560
cctggagaat ggtgaacctg agactagagc ccagagtggg gcctgcctgt tgggagtttg    7620
tctatcttgt gttgtgtggg gagggagagc ccaggtctgt atgtccggag ggatctgggc    7680
tggcacttac cccacttgct ctcatcaccc tgcaggtgct tctcgagtgt ggggcgcagt    7740
```

-continued

```
ggagggatgc aggtggtctc cctggcgccc acgtgtctcc agaagggccg gggcattgtc    7800
cttcatgagc tcatgcatgt gctgggcttc tggcacgagc acacgcgggc cgaccgggac    7860
cgctatatcc gtgtcaactg gaacgagatc ctgccaggtg agccaggcca cacgcaggac    7920
aggctggtgc cggggagggg acagcacggc ttgggcccaa gtcgcctggt ccccatgggt    7980
gaggctatcc atcctcccca tcacctgcct gcttcctgtg gggaaggtgg gggtctcact    8040
tctgtctggt acctggtacc tggaggtggt actctggggt ctgctctggg ccccaggcct    8100
tcctctaccc acctgtagtt gtgccttagc tagggcgcca ccacctgctt tgtctcgctt    8160
ctcatccctg acactgtcct ctccctggcg atggggcagg cagtgcccat gatacctgct    8220
tgttgagtac tctagcagcg gtctcatgta ccagatacca ccaccatgga ctggggctgt    8280
gtgccagctt gggagctga gccaaagtgg daccccaagg tagcaggctg cacaagccaa    8340
gtgctgggcc acgggctgag ggcagcactg tgggctgggg acatgtgcca gtggtgccag    8400
tgagcaggca gaaggaacac agactgtggc catgggagag tggaggctgg aggcaggtgg    8460
gctgtggttc ctgtgctggc agcggctgtg tggcgccggg gatcagatcc tggtgatggt    8520
ggggtctctc tcattgtggg cttgatggtc tggttcagga ggcaggaaga gccccacgag    8580
ggaggggcag aggaggtttg ggtgggagtc tggcttaggg gttggagcag aaggcctac     8640 cgcaggtgga gggcgtccag cacgagacct ttcaggctg tcatgttagc caggtgaggc     8700
agccagggaa gctgcctggg cccaaggacc ttcccaggcc ccaaacaccg ctttctcagt    8760
ggctctcagc aaacatgagt cacagagaaa ggggtgacgg ggcacgtggg tagcacctca    8820
caaaggggga ggggatggat attgaatcag accaggctgg ggaggttgtg aggggggtga    8880
caagtgactc tgtaccctga aaacagactg atccttccca atgctcgtgg aacagttgtg    8940
aaagtttacc ctgataattt tatgatatac catgaaatgc catgaaaacc tgcaactctg    9000
aaagtagacc aatgtaaaca ttctgatcat gatataaagt agaaaccgat acatcaaaac    9060
cgaaagcttc tcctattcag aaattgaaaa aaacaacaaa actttctttc agctctggag    9120
ttaaagtaca gcaattctaa aaaaaaatca tgaaagacta gaaaagccaa tggttcacag    9180
ctaaagcaat gctcagagaa aatgtgtaga cttacgtatc agtaaacaga acaaattgag    9240
catgtcaacc caagttaaat gaaagcagga gggaatttca aaaggtaaaa gcagaaattg    9300
agttggaaaa cagcactaat aattattcct aatgataaaa caggctaaaa cacgggttcc    9360
ccagtggaaa aaatgagaac atatttgttc ccatttaggt taatatgttc tcattaggtt    9420
aacatgtaca gaaactgcca gggcagacac attaataaca gtaattaact gttgtggggc    9480
ggggaggtgg gaactcagga agcagggat ggaatagact tttactacat ctcaatattt     9540
gacttttgaa ccaaatgaat atactactta ttcaaaagta tgtttaatga attttttaaaa   9600 agaagtaaga gctcaagagg cagctatgtt aggcaggtgg tggggtatga aggtgctgga    9660
gggctcattt gctccatgga gaggaagctg ctgtgaccga ggtggcgtgt atgcgtggct    9720
ggctggctgg atttgggagg attgggggag caatccctct gaaggcctgg gggacttgag    9780 tgaggggag atgggctcca aatctgggga agtgttgtgg cctgacacag gaagaacagg     9840
tgggcctgtg actggggact agggcatcac cactgcagat gacagcgtgg cagcttttta    9900
aagctgggtc aaggaataga catttcatct ggggtgggag ggacatctga gaccctgagc    9960
agtgtgggac ccgtggcagc tgtggcttat gcagagacca gccccgtgca gactgaatat   10020
gcaaggagga aggatgggtg gagggaacag ctaggaggtg atggttggcc agccatgggg   10080
tccctgtgcc tctacctcaa ctagtacagg ttggggatcc tcccagggct gggaaagtgg   10140
```

-continued

```
gactggtacc agaagcagca tggtggctgt gggctcagcc cctcagcttg ggtgagttat    10200
gagctcccag aagactctcc cagccattgc ctgcccttc ttgcctgccc tctttatata    10260
tcagtaagtt gtattgtttt tgtattttta ggctttgaaa tcaacttcat caagtctcgg    10320
agcagcaaca tgctgacgcc ctatgactac tcctctgtga tgcactatgg gaggtgagga    10380
ccctgccttc ttctccctct gcttccccca gcctctcccg tggtgatctg gactcagggg    10440
tctcccgctg ggttccaggc tcgccttcag ccggcgtggg ctgcccacca tcacaccact    10500
ttgggccccc agtgtccaca tcggccagcg atggaacctg agtgcctcgg acatcacccg    10560
ggtcctcaaa ctctacggct gcagcccaag tggccccagg ccccgtggga gaggtgagtg    10620
gcatggcagg aaggtgactt gaacctggag aaggcgcctg tgctctaatg gtgtcaggga    10680
gggtgacaag gagggagatg aggttgcagg gggagcaggg tgagatcacg ggggcttgcc    10740
acaacgacgc agaacaagca cttgaggaaa gttaacactc actatgactc aactgtaacc    10800
aaagaggaat agggctcact tgcttagcct agataataaa catctaccaa aaacctagaa    10860
caaaagttaa gggtaaaaca ttaaaactgg gaccaagaca agttttccca ccattgtccc    10920
atctactcca cattgtgtgg cagtggaggt cctgggcacc gaggtagagc caaagaaact    10980
aaaggtccga ggattggaaa ggaagcaaaa aaatcgttca taatagatga ttacctgtat    11040
tgaaagcaac aatctataaa caagttatta gaactaataa gaattagaaa aggtaaatac    11100
agttaatata aaaatcatat ttctgtacac ccagttagaa aacacaattg ttagtaaaca    11160
taccattata atagcaatca taaaggtccc aaggaataaa tctgacagct gtatcaaaca    11220
tttgaggaaa aatgaacctt tattaaaatc gttaaataat acttaaatat agataaatct    11280
gttattgaaa ggaaggcaat gttataaaaa ttcagtcttc ccaaattaat ctataaattc    11340
ccactcaaaa taagtttgat cttgacagag tgattttttt tttctttttt tttttttaaag    11400 atggagtctc actctgtcac ccaggctgga gtgcagtggc acaatctcgg ctcactgcag    11460
tctctgcctc cgaggttcaa gtgattcttg tgcctcaatc tcctgagcag ctgggcttac    11520
aggtgcgtgc caccacaccc aactaatttt tgtatttta gtggggacag ggtttcacca    11580
tgttggccag gctggtcttg aactcctgac cgcaagtgat gcgcctgcct ggcctcccg    11640 attgacaggg tgattataaa gttttttatat gagaatatga aaggtcaata atagccaaga    11700
catccctgaa ggaaaaacta aaaagacttg tcctagcaga tgttagtcat ctagttcatg    11760
aaacgtcttt acataaatgc atagcactgg agcaaggcta acaattgcc cgctggaaca    11820 gaatcaaatt tagaaacaga ttccattcag aagcagagcc ttgatgaagg gccattgatg    11880
gtcactatgg aaggacagtt aagttactta gttgtcttag agccatttag catctattta    11940
aaaatcccta actcatatca tgcgcaaata actctggatg catgaaagac acatgtaata    12000
aaaactttaa catgtttaga aaaaaatat atagtaagat ctcttcatga ccttgggata    12060
gggaaggatc acttaaatga gatacagcac taattgtaaa actagaaaga ttcataaatt    12120
caactacatt aattataact ttgtccaaag gcaccaaaaa gaaagtgaaa atacaggtta    12180
caaatagact tttttttttt tttttgaga cagtttcact cttttgccc aggctggagt    12240 gcaatggcac gatcttggct cactgcaact tctgcctccc aggttcaagt gattctcctg    12300
cgtcagcctc ccttgtagct gggattacag tcacgcacca ccatgcctgg ctaattttgt    12360 attttttatta gagatggggt ttcaccatgt tggctaggct ggtcttgagc tcctgacctc    12420
aggtgatccc cctgcctcag cttcccaaag tgctgggatt acaggtgtga gccactgtgc    12480
```

```
ctggccccaa tatatttttt tgcaacacat aatttgtata caaaatacat aaagaactac    12540
acattaatat aagaacaaac cagctgagtg tgatggctca tgcctgtaat cacagcactt    12600
tgggaggctg aggtgggtgg atcgcttgag cttaggagtt c                       12641
```

<210> SEQ ID NO 4
<211> LENGTH: 268
<212> TYPE: PRT
<213> ORGANISM: Japanese medaka

<400> SEQUENCE: 4

```
Leu Leu Phe Leu Leu Gly Ile Ala Gln Ala Leu Pro Val Gln Asn Glu
 1               5                  10                  15

Glu Gly His Glu Glu Gly Asn Lys Glu Gly His Gly Glu Glu Gly Val
            20                  25                  30

Glu Glu Gly Asp Glu Asp Asp Phe Val Asp Phe Thr Thr Arg Ile Leu
        35                  40                  45

Thr Ser Asn Asn Asn Thr Asp Gln Leu Leu Glu Gly Asp Leu Val
    50                  55                  60

Ala Pro Thr Asn Arg Asn Ala Met Lys Cys Trp Tyr Asn Ser Cys Phe
65                  70                  75                  80

Trp Lys Lys Ala Ser Asn Gly Phe Val Val Ile Pro Tyr Val Ile Ser
                85                  90                  95

Ser Gln Tyr Ser Arg Gly Glu Val Ala Thr Ile Glu Gly Ala Met Arg
            100                 105                 110

Ala Phe Asn Gly Arg Thr Cys Ile Arg Phe Val Arg Arg Thr Asn Glu
        115                 120                 125

Tyr Asp Phe Ile Ser Val Val Ser Lys Asn Gly Cys Tyr Ser Glu Leu
    130                 135                 140

Gly Arg Lys Gly Gly Gln Gln Glu Leu Ser Leu Asn Arg Gly Gly Cys
145                 150                 155                 160

Met Tyr Ser Gly Ile Ile Gln His Glu Leu Asn His Ala Leu Gly Phe
                165                 170                 175

Gln His Glu Gln Thr Arg Ser Asp Arg Asp Ser Tyr Val Arg Ile Asn
            180                 185                 190

Trp Gln Asn Ile Ile Pro Ala Ser Ala Tyr Asn Phe Asn Lys His Asp
        195                 200                 205

Thr Asn Asn Leu Asn Thr Pro Tyr Asp Tyr Ser Ser Ile Met His Tyr
    210                 215                 220

Gly Arg Asp Ala Phe Ser Ile Ala Tyr Gly Arg Asp Ser Ile Thr Pro
225                 230                 235                 240

Ile Pro Asn Pro Asn Val Pro Ile Gly Gln Arg Asn Gly Met Ser Arg
                245                 250                 255

Trp Asp Ile Thr Arg Ile Asn Val Leu Tyr Asn Cys
            260                 265
```

<210> SEQ ID NO 5
<211> LENGTH: 239
<212> TYPE: PRT
<213> ORGANISM: Oryzias latipes

<400> SEQUENCE: 5

```
Glu Gly His Glu Glu Gly Asp Glu Asp Asp Phe Val Asp Ile Thr Thr
 1               5                  10                  15

Arg Ile Leu Thr Ser Asn Asn Asn Thr Asp Gln Leu Leu Glu Gly
            20                  25                  30
```

-continued

```
Asp Leu Val Ala Pro Thr Asn Arg Asn Ala Met Lys Cys Trp Ser Ser
    35              40              45

Ser Cys Phe Trp Lys Lys Ala Ser Asn Gly Leu Val Val Ile Pro Tyr
50              55              60

Val Ile Ser Ser Glu Tyr Ser Gly Gly Glu Val Ala Thr Ile Glu Gly
65              70              75              80

Ala Met Arg Ala Phe Asn Gly Lys Thr Cys Ile Arg Phe Val Arg Arg
            85              90              95

Thr Asn Glu Tyr Asp Phe Ile Ser Val Val Ser Lys Thr Gly Cys Tyr
            100             105             110

Ser Glu Leu Gly Arg Lys Gly Gly Leu Gln Glu Leu Ser Ile Asn Arg
        115             120             125

Gly Gly Cys Met Tyr Ser Gly Ile Ile Gln His Glu Leu Asn His Ala
        130             135             140

Leu Gly Phe Gln His Glu Gln Thr Arg Ser Asp Arg Asp Ser Tyr Val
145             150             155             160

Arg Ile Asn Trp Glu Asn Ile Ile Pro Ala Ser Ala Tyr Asn Phe Asn
                165             170             175

Lys Gln Asp Thr Asn Asn Leu Asn Thr Pro Tyr Asp Tyr Ser Ser Ile
            180             185             190

Met His Tyr Gly Lys Asp Ala Phe Ser Ile Ala Tyr Gly Arg Asp Ser
        195             200             205

Ile Thr Pro Ile Pro Asn Pro Asn Val Pro Ile Gly Gln Arg Asn Gly
        210             215             220

Met Ser Arg Trp Asp Ile Thr Arg Ile Asn Val Leu Tyr Asn Cys
225             230             235
```

ISOLATED HUMAN SECRETED PROTEINS, NUCLEIC ACID MOLECULES ENCODING HUMAN SECRETED PROTEINS, AND USES THEREOF

FIELD OF THE INVENTION

The present invention is in the field of secreted proteins that are related to the choriolytic enzyme subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Secreted Proteins

Many human proteins serve as pharmaceutically active compounds. Several classes of human proteins that serve as such active compounds include hormones, cytokines, cell growth factors, and cell differentiation factors. Most proteins that can be used as a pharmaceutically active compound fall within the family of secreted proteins. It is, therefore, important in developing new pharmaceutical compounds to identify secreted proteins that can be tested for activity in a variety of animal models. The present invention advances the state of the art by providing many novel human secreted proteins.

Secreted proteins are generally produced within cells at rough endoplasmic reticulum, are then exported to the golgi complex, and then move to secretory vesicles or granules, where they are secreted to the exterior of the cell via exocytosis.

Secreted proteins are particularly useful as diagnostic markers. Many secreted proteins are found, and can easily be measured, in serum. For example, a 'signal sequence trap' technique can often be utilized because many secreted proteins, such as certain secretory breast cancer proteins, contain a molecular signal sequence for cellular export. Additionally, antibodies against particular secreted serum proteins can serve as potential diagnostic agents, such as for diagnosing cancer.

Secreted proteins play a critical role in a wide array of important biological processes in humans and have numerous utilities; several illustrative examples are discussed herein. For example, fibroblast secreted proteins participate in extracellular matrix formation. Extracellular matrix affects growth factor action, cell adhesion, and cell growth. Structural and quantitative characteristics of fibroblast secreted proteins are modified during the course of cellular aging and such aging related modifications may lead to increased inhibition of cell adhesion, inhibited cell stimulation by growth factors, and inhibited cell proliferative ability (Eleftheriou et al., *Mutat Res* 1991 March–November; 256 (2–6):127–38).

The secreted form of amyloid beta/A4 protein precursor (APP) functions as a growth and/or differentiation factor. The secreted form of APP can stimulate neurite extension of cultured neuroblastoma cells, presumably through binding to a cell surface receptor and thereby triggering intracellular transduction mechanisms. (Roch et al., *Ann N Y Acad Sci* 1993 Sep. 24; 695:149–57). Secreted APPs modulate neuronal excitability, counteract effects of glutamate on growth cone behaviors, and increase synaptic complexity. The prominent effects of secreted APPs on synaptogenesis and neuronal survival suggest that secreted APPs play a major role in the process of natural cell death and, furthermore, may play a role in the development of a wide variety of neurological disorders, such as stroke, epilepsy, and Alzheimer's disease (Mattson et al., *Perspect Dev Neurobiol* 1998; 5(4):337–52).

Breast cancer cells secrete a 52K estrogen-regulated protein (see Rochefort et al., *Ann N Y Acad Sci* 1986; 464: 190–201). This secreted protein is therefore useful in breast cancer diagnosis.

Two secreted proteins released by platelets, platelet factor 4 (PF4) and beta-thromboglobulin (betaTG), are accurate indicators of platelet involvement in hemostasis and thrombosis and assays that measure these secreted proteins are useful for studying the pathogenesis and course of thromboembolic disorders (Kaplan, *Adv Exp Med Biol* 1978; 102:105–19).

Vascular endothelial growth factor (VEGF) is another example of a naturally secreted protein. VEGF binds to cell-surface heparan sulfates, is generated by hypoxic endothelial cells, reduces apoptosis, and binds to high-affinity receptors that are up-regulated by hypoxia (Asahara et al., *Semin Interv Cardiol* 1996 September; 1(3):225–32).

Many critical components of the immune system are secreted proteins, such as antibodies, and many important functions of the immune system are dependent upon the action of secreted proteins. For example, Saxon et al., *Biochem Soc Trans* 1997 May; 25(2):383–7, discusses secreted IgE proteins.

For a further review of secreted proteins, see Nilsen-Hamilton et al., *Cell Biol Int Rep* 1982 September; 6(9): 815–36.

The present invention has substantial similarity to choriolytic enzyme, Choriolysin. Choriolytic enzyme, is part of the hatching enzyme of the teleost, Oryzias latipes. There are two parts of this enzyme, one is high choriolytic enzyme (choriolysin H, HCE) and the other one is low choriolytic enzyme (choriolysin L, LCE). Choriolytic enzyme is similar in some enzymological characteristics and protein structure (55% identity in amino acid sequence) and belong to the astacin family.

The genes for HCE and LCE have been in isolated from the genomic library constructed from DNA of the inbred drR strain fish. In contrast to the close similarity of the enzymes, there was a marked difference in their gene organization. The LCE gene was a single copy gene and composed of eight exons interrupted by seven introns. The HCE genes were multicopy genes and lacked introns. In the haploid genome of the drR strain fish, there are eight HCE genes. 5'flanking regions of the LCE gene and the HCE genes had consensus TATA box sequences, but not CAT box nor GC box sequences. For more information related to the present invention, see Yasumasu et al., Eur J Biochem 1996 May 1;237(3):752–8.

Secreted proteins, particularly members of the choriolytic enzyme protein subfamily, are a major target for drug action and development. Accordingly, it is valuable to the field of pharmaceutical development to identify and characterize previously unknown members of this subfamily of secreted proteins. The present invention advances the state of the art by providing previously unidentified human secreted proteins that have homology to members of the choriolytic enzyme protein subfamily.

SUMMARY OF THE INVENTION

The present invention is based in part on the identification of amino acid sequences of human secreted peptides and proteins that are related to the choriolytic enzyme protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate secreted protein activity in cells and tissues that express the secreted protein.

DESCRIPTION OF THE FIGURE SHEETS

FIG. 1 provides the nucleotide sequence of a cDNA molecule or transcript sequence that encodes the secreted protein of the present invention. (SEQ ID NO:1) In addition, structure and functional information is provided, such as ATG start, stop and tissue distribution, where available, that allows one to readily determine specific uses of inventions based on this molecular sequence.

FIG. 2(A–C) provides the predicted amino acid sequence of the secreted protein of the present invention. (SEQ ID NO:2) In addition structure and functional information such as protein family, function, and modification sites is provided where available, allowing one to readily determine specific uses of inventions based on this molecular sequence.

FIG. 3(A–G) provides genomic sequences that span the gene encoding the secreted protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 6 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a secreted protein or part of a secreted protein and are related to the choriolytic enzyme protein subfamily. Utilizing these sequences, additional genomic sequences were assembled and transcript and/or cDNA sequences were isolated and characterized. Based on this analysis, the present invention provides amino acid sequences of human secreted peptides and proteins that are related to the choriolytic enzyme protein subfamily, nucleic acid sequences in the form of transcript sequences, cDNA sequences and/or genomic sequences that encode these secreted peptides and proteins, nucleic acid variation (allelic information), tissue distribution of expression, and information about the closest art known protein/peptide/domain that has structural or sequence homology to the secreted protein of the present invention.

In addition to being previously unknown, the peptides that are provided in the present invention are selected based on their ability to be used for the development of commercially important products and services. Specifically, the present peptides are selected based on homology and/or structural relatedness to known secreted proteins of the choriolytic enzyme protein subfamily and the expression pattern observed. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known choriolytic enzyme family or subfamily of secreted proteins.

Specific Embodiments

Peptide Molecules

The present invention provides nucleic acid sequences that encode protein molecules that have been identified as being members of the secreted protein family of proteins and are related to the choriolytic enzyme protein subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the secreted peptides of the present invention, secreted peptides, or peptides/proteins of the present invention.

The present invention provides isolated peptide and protein molecules that consist of, consist essentially of, or comprise the amino acid sequences of the secreted peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the secreted peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated secreted peptide can be purified from cells that naturally express it, purified from cells that have been altered to express it (recombinant), or synthesized using known protein synthesis methods. For example, a nucleic acid molecule encoding the secreted peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the secreted peptides of the present invention are the naturally occurring mature proteins. A brief description of how various types of these proteins can be made/isolated is provided below.

The secreted peptides of the present invention can be attached to heterologous sequences to form chimeric or fusion proteins. Such chimeric and fusion proteins comprise a secreted peptide operatively linked to a heterologous protein having an amino acid sequence not substantially homologous to the secreted peptide. "Operatively linked" indicates that the secreted peptide and the heterologous protein are fused in-frame. The heterologous protein can be fused to the N-terminus or C-terminus of the secreted peptide.

In some uses, the fusion protein does not affect the activity of the secreted peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant secreted peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A secreted peptide-encoding nucleic acid can be cloned into such an expression vector such that the fusion moiety is linked in-frame to the secreted peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the secreted peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and*

Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., Nucleic Acids Res. 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (J. Mol. Biol. 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (Nucleic Acids Res. 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the secreted peptides of the present invention as well as being encoded by the same genetic locus as the secreted peptide provided herein.

Allelic variants of a secreted peptide can readily be identified as being a human protein having a high degree (significant) of sequence homology/identity to at least a portion of the secreted peptide as well as being encoded by the same genetic locus as the secreted peptide provided herein. Genetic locus can readily be determined based on the genomic information provided in FIG. 3, such as the genomic sequence mapped to the reference human. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a secreted peptide encoding nucleic acid molecule under stringent conditions as more fully described below.

FIG. 3 provides information on SNPs that have been found in the gene encoding the secreted protein of the present invention. SNPs were identified at 6 different nucleotide positions in introns and regions 5' and 3' of the ORF. Such SNPs in introns and outside the ORF may affect control/regulatory elements. One occurred at coding region may change the secondary structure of the protein. The changes in the amino acid sequence that these SNPs cause can readily be determined using the universal genetic code and the protein sequence provided in FIG. 2 as a base.

Paralogs of a secreted peptide can readily be identified as having some degree of significant sequence homology/identity to at least a portion of the secreted peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a secreted peptide encoding nucleic acid molecule under moderate to stringent conditions as more fully described below.

Orthologs of a secreted peptide can readily be identified as having some degree of significant sequence homology/identity to at least a portion of the secreted peptide as well as being encoded by a gene from another organism. Preferred orthologs will be isolated from mammals, preferably primates, for the development of human therapeutic targets and agents. Such orthologs will be encoded by a nucleic acid sequence that will hybridize to a secreted peptide encoding nucleic acid molecule under moderate to stringent conditions, as more fully described below, depending on the degree of relatedness of the two organisms yielding the proteins.

Non-naturally occurring variants of the secreted peptides of the present invention can readily be generated using recombinant techniques. Such variants include, but are not limited to deletions, additions and substitutions in the amino acid sequence of the secreted peptide. For example, one class of substitutions are conserved amino acid substitution. Such substitutions are those that substitute a given amino acid in a secreted peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306–1310 (1990).

Variant secreted peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as secreted protein activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the secreted peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a secreted peptide. Such fragments can be chosen based on the ability to retain one or more of the biological activities of the secreted peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the secreted peptide, e.g., active site or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in secreted peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (Ann. N.Y. Acad. Sci. 663:48–62 (1992)).

Accordingly, the secreted peptides of the present invention also encompass derivatives or analogs in which a substituted amino acid residue is not one encoded by the genetic code, in which a substituent group is included, in which the mature secreted peptide is fused with another compound, such as a compound to increase the half-life of the secreted peptide (for example, polyethylene glycol), or in which the additional amino acids are fused to the mature secreted peptide, such as a leader or secretory sequence or a sequence for purification of the mature secreted peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a secreted protein-effector protein interaction or secreted protein-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, secreted proteins isolated from humans and their human/mammalian orthologs serve as targets for identifying agents for use in mammalian therapeutic applications, e.g. a human drug, particularly in modulating a biological or pathological response in a cell or tissue that expresses the secreted protein. A large percentage of pharmaceutical agents are being developed that modulate the activity of secreted proteins, particularly members of the choriolytic enzyme subfamily (see Background of the Invention). The structural and functional information provided in the Background and Figures provide specific and substantial uses for the molecules of the present invention, particularly in combination with the expression information provided in FIG. 1. Such uses can readily be determined using the information provided herein, that which is known in the art, and routine experimentation.

The proteins of the present invention (including variants and fragments that may have been disclosed prior to the present invention) are useful for biological assays related to secreted proteins that are related to members of the choriolytic enzyme subfamily. Such assays involve any of the known secreted protein functions or activities or properties useful for diagnosis and treatment of secreted protein-related conditions that are specific for the subfamily of secreted proteins that the one of the present invention belongs to, particularly in cells and tissues that express the secreted protein.

The proteins of the present invention are also useful in drug screening assays, in cell-based or cell-free systems. Cell-based systems can be native, i.e., cells that normally express the secreted protein, as a biopsy or expanded in cell culture. In an alternate embodiment, cell-based assays involve recombinant host cells expressing the secreted protein.

The polypeptides can be used to identify compounds that modulate secreted protein activity of the protein in its natural state or an altered form that causes a specific disease or pathology associated with the secreted protein. Both the secreted proteins of the present invention and appropriate variants and fragments can be used in high-throughput screens to assay candidate compounds for the ability to bind to the secreted protein. These compounds can be further screened against a functional secreted protein to determine the effect of the compound on the secreted protein activity. Further, these compounds can be tested in animal or invertebrate systems to determine activity/effectiveness. Compounds can be identified that activate (agonist) or inactivate (antagonist) the secreted protein to a desired degree.

Further, the proteins of the present invention can be used to screen a compound for the ability to stimulate or inhibit interaction between the secreted protein and a molecule that normally interacts with the secreted protein, e.g. a substrate or a component of the signal pathway that the secreted protein normally interacts (for example, another secreted protein). Such assays typically include the steps of combining the secreted protein with a candidate compound under conditions that allow the secreted protein, or fragment, to interact with the target molecule, and to detect the formation of a complex between the protein and the target or to detect the biochemical consequence of the interaction with the secreted protein and the target.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant secreted proteins or appropriate fragments containing mutations that affect secreted protein function and thus compete for substrate. Accordingly, a fragment that competes for substrate, for example with a higher affinity, or a fragment that binds substrate but does not allow release, is encompassed by the invention.

Any of the biological or biochemical functions mediated by the secreted protein can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the secreted protein can be assayed.

Binding and/or activating compounds can also be screened by using chimeric secreted proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native secreted protein. Accordingly, a different set of signal transduction components is available as an end-point assay for activation. This allows for assays to be performed in other than the specific host cell from which the secreted protein is derived.

The proteins of the present invention are also useful in competition binding assays in methods designed to discover compounds that interact with the secreted protein (e.g. binding partners and/or ligands). Thus, a compound is exposed to a secreted protein polypeptide under conditions that allow the compound to bind or to otherwise interact with the polypeptide. Soluble secreted protein polypeptide is also added to the mixture. If the test compound interacts with the soluble secreted protein polypeptide, it decreases the amount of complex formed or activity from the secreted protein target. This type of assay is particularly useful in cases in which compounds are sought that interact with specific regions of the secreted protein. Thus, the soluble polypeptide that competes with the target secreted protein region is designed to contain peptide sequences corresponding to the region of interest.

To perform cell free drug screening assays, it is sometimes desirable to immobilize either the secreted protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of secreted protein-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a secreted protein-binding protein and a candidate compound are incubated in the secreted protein-presenting wells and the amount of complex trapped in the well can be quantitated. Methods for detecting such complexes, in addition to those described above for the GST-immobilized complexes, include immunodetection of complexes using antibodies reactive with the secreted protein target molecule, or which are reactive with secreted protein and compete with the target molecule, as well as enzyme-linked assays which rely on detecting an enzymatic activity associated with the target molecule.

Agents that modulate one of the secreted proteins of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of secreted protein activity identified according to these drug screening assays can be used to treat a subject with a disorder mediated by the secreted protein pathway, by treating cells or tissues that express the secreted protein. These methods of treatment include the steps of administering a modulator of secreted protein activity in a pharmaceutical composition to a subject in need of such treatment, the modulator being identified as described herein.

In yet another aspect of the invention, the secreted proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the secreted protein and are involved in secreted protein activity.

The two-hybrid system is based on the modular nature of most transcription factors, which consist of separable DNA-binding and activation domains. Briefly, the assay utilizes two different DNA constructs. In one construct, the gene that codes for a secreted protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a secreted protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the secreted protein.

This invention further pertains to novel agents identified by the above-described screening assays. Accordingly, it is within the scope of this invention to further use an agent identified as described herein in an appropriate animal model. For example, an agent identified as described herein (e.g., a secreted protein-modulating agent, an antisense secreted protein nucleic acid molecule, a secreted protein-specific antibody, or a secreted protein-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The secreted proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. The method involves contacting a biological sample with a compound capable of interacting with the secreted protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered secreted protein activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the secreted protein in which one or more of the secreted protein functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and secreted protein activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Accordingly, methods for treatment include the use of the secreted protein or fragments.

Antibodies

The invention also provides antibodies that selectively bind to one of the peptides of the present invention, a protein comprising such a peptide, as well as variants and fragments thereof As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the secreted proteins. Antibodies can be prepared from any region of the peptide as described herein. However, preferred regions will include those involved in function/activity and/or secreted protein/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Thus, where a specific protein has been correlated with expression in a specific tissue, antibodies that are specific for this protein can be used to identify a tissue type.

The antibodies are also useful for inhibiting protein function, for example, blocking the binding of the secreted peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a secreted peptide or protein of the present invention (cDNA, transcript and genomic sequence). Such nucleic acid molecules will consist of, consist essentially of, or comprise a nucleotide sequence that encodes one of the secreted peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the secreted peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the secreted proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

FIG. 3 provides information on SNPs that have been found in the gene encoding the secreted protein of the present invention. SNPs were identified at 6 different nucleotide positions in introns and regions 5' and 3' of the ORF. Such SNPs in introns and outside the ORF may affect control/regulatory elements. One occurred at coding region may change the secondary structure of the protein. The changes in the amino acid sequence that these SNPs cause can readily be determined using the universal genetic code and the protein sequence provided in FIG. 2 as a base.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 6 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in secreted protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a secreted protein, such as by measuring a level of a secreted protein-encoding nucleic acid in a sample of cells from a subject e.g., mRNA or genomic DNA, or determining if a secreted protein gene has been mutated.

Nucleic acid expression assays are useful for drug screening to identify compounds that modulate secreted protein nucleic acid expression.

The invention thus provides a method for identifying a compound that can be used to treat a disorder associated with nucleic acid expression of the secreted protein gene, particularly biological and pathological processes that are mediated by the secreted protein in cells and tissues that express it. The method typically includes assaying the ability of the compound to modulate the expression of the secreted protein nucleic acid and thus identifying a compound that can be used to treat a disorder characterized by undesired secreted protein nucleic acid expression. The assays can be performed in cell-based and cell-free systems. Cell-based assays include cells naturally expressing the secreted protein nucleic acid or recombinant cells genetically engineered to express specific nucleic acid sequences.

Thus, modulators of secreted protein gene expression can be identified in a method wherein a cell is contacted with a candidate compound and the expression of mRNA determined. The level of expression of secreted protein mRNA in the presence of the candidate compound is compared to the level of expression of secreted protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate secreted protein nucleic acid expression in cells and tissues that express the secreted protein. Modulation includes both up-regulation (i.e. activation or agonization) or down-regulation (suppression or antagonization) or nucleic acid expression.

Alternatively, a modulator for secreted protein nucleic acid expression can be a small molecule or drug identified using the screening assays described herein as long as the drug or small molecule inhibits the secreted protein nucleic acid expression in the cells and tissues that express the protein.

The nucleic acid molecules are also useful for monitoring the effectiveness of modulating compounds on the expression or activity of the secreted protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in secreted protein nucleic acid expression, and particularly in qualitative changes that lead to pathology. The nucleic acid molecules can be used to detect mutations in secreted protein genes and gene expression products such as mRNA. The nucleic acid molecules can be used as hybridization probes to detect naturally occurring genetic mutations in the secreted protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the secreted protein gene associated with a dysfunction provides a diagnostic tool for an active disease or susceptibility to disease when the disease results from overexpression, underexpression, or altered expression of a secreted protein.

Individuals carrying mutations in the secreted protein gene can be detected at the nucleic acid level by a variety of techniques. FIG. 3 provides information on SNPs that have been found in the gene encoding the secreted protein of the present invention. SNPs were identified at 6 different nucleotide positions in introns and regions 5' and 3' of the ORF. Such SNPs in introns and outside the ORF may affect control/regulatory elements. One occurred at coding region may change the secondary structure of the protein. The changes in the amino acid sequence that these SNPs cause can readily be determined using the universal genetic code and the protein sequence provided in FIG. 2 as a base. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a secreted protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant secreted protein gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the secreted protein gene in an individual in order to select an appropriate compound or dosage regimen for treatment. FIG. 3 provides information on SNPs that have been found in the gene encoding the secreted protein of the present invention. SNPs were identified at 6 different nucleotide positions in introns and regions 5' and 3' of the ORF. Such SNPs in introns and outside the ORF may affect control/regulatory elements. One occurred at coding region may change the secondary structure of the protein. The changes in the amino acid sequence that these SNPs cause can readily be determined using the universal genetic code and the protein sequence provided in FIG. 2 as a base.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control secreted protein gene expression in cells, tissues, and organisms. A DNA antisense nucleic acid molecule is designed to be complementary to a region of the gene involved in transcription, preventing transcription and hence production of secreted protein. An antisense RNA or DNA nucleic acid molecule would hybridize to the mRNA and thus block translation of mRNA into secreted protein.

Alternatively, a class of antisense molecules can be used to inactivate mRNA in order to decrease expression of secreted protein nucleic acid. Accordingly, these molecules can treat a disorder characterized by abnormal or undesired secreted protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the secreted protein, such as substrate binding.

The nucleic acid molecules also provide vectors for gene therapy in patients containing cells that are aberrant in secreted protein gene expression. Thus, recombinant cells, which include the patient's cells that have been engineered ex vivo and returned to the patient, are introduced into an individual where the cells produce the desired secreted protein to treat the individual.

The invention also encompasses kits for detecting the presence of a secreted protein nucleic acid in a biological sample. For example, the kit can comprise reagents such as a labeled or labelable nucleic acid or agent capable of detecting secreted protein nucleic acid in a biological sample; means for determining the amount of secreted protein nucleic acid in the sample; and means for comparing the amount of secreted protein nucleic acid in the sample with a standard. The compound or agent can be packaged in a suitable container. The kit can further comprise instructions for using the kit to detect secreted protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the secreted proteins/ peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the secreted protein gene of the present invention. FIG. 3 provides information on SNPs that have been found in the gene encoding the secreted protein of the present invention. SNPs were identified at 6 different nucleotide positions in introns and regions 5' and 3' of the ORF. Such SNPs in introns and outside the ORF may affect control/regulatory elements. One occurred at coding region may change the secondary structure of the protein. The changes in the amino acid sequence that these SNPs cause can readily be determined using the universal genetic code and the protein sequence provided in FIG. 2 as a base.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified secreted protein gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al.,*EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a secreted protein or peptide that can be further purified to produce desired amounts of secreted protein or fragments. Thus, host cells containing expression vectors are useful for peptide production.

Host cells are also useful for conducting cell-based assays involving the secreted protein or secreted protein fragments, such as those described above as well as other formats known in the art. Thus, a recombinant host cell expressing a native secreted protein is useful for assaying compounds that stimulate or inhibit secreted protein function.

Host cells are also useful for identifying secreted protein mutants in which these functions are affected. If the mutants naturally occur and give rise to a pathology, host cells containing the mutations are useful to assay compounds that have a desired effect on the mutant secreted protein (for example, stimulating or inhibiting function) which may not be indicated by their effect on the native secreted protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a secreted protein and identifying and evaluating modulators of secreted protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the secreted protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the secreted protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, secreted protein activation, and signal transduction, may not be evident from in vitro cell-free or cell-based assays. Accordingly, it is useful to provide non-human transgenic animals to assay in vivo secreted protein function, including substrate interaction, the effect of specific mutant secreted proteins on secreted protein function and substrate interaction, and the effect of chimeric secreted proteins. It is also possible to assess the effect of null mutations, that is, mutations that substantially or completely eliminate one or more secreted protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule, wherein the nucleotide sequence of said nucleic acid molecule consists of a nucleotide sequence selected from the group consisting of:
   (a) a nucleotide sequence that encodes a polypeptide having an amino acid sequence comprising SEQ ID NO:2 except that residue 222 is glutamine;
   (b) a nucleotide sequence consisting of SEQ ID NO:1 except that nucleotide 665 is adenine;
   (c) a nucleotide sequence consisting of SEQ ID NO:3 except that nucleotide 10319 is adenine; and
   (d) a nucleotide sequence that is completely complementary to a nucleotide sequence of (a)–(c).

2. A vector comprising the nucleic acid molecule of claim 1.

3. An isolated host cell containing the vector of claim 2.

4. A process for producing a polypeptide comprising culturing an isolated host cell under conditions sufficient for the production of said polypeptide, wherein said host cell comprises a vector which comprises the nucleic acid of a), b) or c) of claim 1, and recovering said polypeptide.

5. An isolated polynucleotide, wherein the nucleotide sequence of said polynucleotide consists of SEQ ID NO:1 except that nucleotide 665 is adenine; or the complete complement of said nucleotide sequence.

6. An isolated polynucleotide, wherein the nucleotide sequence of said polynucleotide consists of SEQ ID NO:3 except that nucleotide 10319 is adenine, or the complete complement of said nucleotide sequence.

7. The vector of claim 2, wherein said vector is selected from the group consisting of a plasmid, a virus, and a bacteriophage.

8. The vector of claim 2, wherein said isolated nucleic acid molecule is inserted into said vector in proper orientation and correct reading frame such that a polypeptide is expressed by a cell transformed with said vector, wherein said polypeptide has an amino acid sequence comprising SEQ ID NO:2 except that residue 222 is glutamine.

9. The vector of claim 8, wherein said isolated nucleic acid molecule is operatively linked to a promoter sequence.

* * * * *